US007166429B2

(12) United States Patent
Van Eijk et al.

(10) Patent No.: US 7,166,429 B2
(45) Date of Patent: Jan. 23, 2007

(54) METHOD FOR GENERATING OLIGONUCLEOTIDES, IN PARTICULAR FOR THE DETECTION OF AMPLIFIED RESTRICTION FRAGMENTS OBTAINED USING AFLP®

(75) Inventors: Michael Josephus Theresia Van Eijk, Herpen (NL); René Cornelis Josephus Hogers, Ede (NL); Leo Heijnen, Vianen (NL)

(73) Assignee: Keygene N.V., Wageningen (NL)

( * ) Notice: Subject to any disclaimer, the term of this patent is extended or adjusted under 35 U.S.C. 154(b) by 553 days.

(21) Appl. No.: 10/169,371

(22) PCT Filed: Dec. 28, 2000

(86) PCT No.: PCT/NL00/00963

§ 371 (c)(1),
(2), (4) Date: Jan. 16, 2003

(87) PCT Pub. No.: WO01/49882

PCT Pub. Date: Jul. 12, 2001

(65) Prior Publication Data

US 2003/0175729 A1 Sep. 18, 2003

(30) Foreign Application Priority Data

Dec. 29, 1999 (EP) .................................. 99204614

(51) Int. Cl.
*C12Q 1/68* (2006.01)
*C12P 19/34* (2006.01)

(52) U.S. Cl. .......................................... 435/6; 435/91.2

(58) Field of Classification Search ..................... None
See application file for complete search history.

(56) References Cited

U.S. PATENT DOCUMENTS 5,710,000 A 1/1998 Sapolsky et al.

FOREIGN PATENT DOCUMENTS

| | | |
|---|---|---|
| EP | 0 534 858 A1 | 3/1993 |
| WO | WO 94/16090 A1 | 7/1994 |
| WO | WO 97/33000 A1 | 9/1997 |
| WO | WO 98/08981 A1 | 3/1998 |
| WO | WO 00/15852 A1 | 3/2000 |
| WO | WO 00/34518 A1 | 6/2000 |
| WO | WO 00/53806 A1 | 9/2000 |

OTHER PUBLICATIONS

Sears et al, Nucleic Acids Res. 24 (18), 3590 (1996).*
Wong et al "General method for HPLC purification and sequencing of selected dsDNA gene fragments from complex PCRs generated during gene expression profiling" BIOTECHNIQUES, vol. 28, No. 4, pp. 776-783, 2000.
Laken et al, "Genotyping by mass spectrometric analysis of short DNA fragments", Nature Biotechnology, vol. 16, pp. 1352-1356, Dec. 1998.
Szybalski et al, "Class IIS restriction enzymes- a review" GENE, vol. 100, pp. 13-26, 1991.
Wu et al, "Time-of-flight mass spectrometry of underivatized single-stranded DNA oligomers by matrix-assisted laser desorption", Anal. Chem., vol. 66, pp. 1637-1645, 1994.
Vos et al, "AFLP: a new technique for DNA fingerprinting" Nucleic Acids Research, vol. 23, No. 21, pp. 4407-4414, 1995.
Douglas Smith, "Ligation-mediated PCR of restriction fragments from large DNA molecules", PCR Methods and Applications, vol. 2, No. 1, pp. 21-27, Aug. 1992.
Douglas Jones, "An iterative and regenerative method for DNA sequencing" BIOTECHNIQUES, vol. 22, No. 5, pp. 938-946, 1997.

* cited by examiner

*Primary Examiner*—James Martinell
(74) *Attorney, Agent, or Firm*—Browdy & Neimark, PLLC

(57) ABSTRACT

The invention relates to a method for generating, and optionally detecting, an oligonucleotide, comprising at least the steps of: a) providing a first dsDNA; b) ligating the first dsDNA to a second dsDNA, in which said second dsDNA sequence comprises within its sequence at least one recognition site for an IIS restriction endonuclease; so as to provide a ligated dsDNA; d) restricting the ligated dsDNA with the at least one restriction endonuclease of the IIS type so as to obtain at least a first and a second IIS-restricted dsDNA; and optionally comprising the further step of: e) detecting the first and/or second IIS-restricted dsDNA obtained in the restriction step d). Preferably, said method comprises the further step of: c) amplifying the ligated dsDNA obtained in the ligating step b) prior to the restriction step d). The detection step e) preferably comprises the steps of: 1) generating at least one ssDNA from either the first or the second IIS-restricted dsDNA obtained in the restriction step d); 2) detecting the at least one ssDNA generated from either the first or the second IIS-restricted dsDNA; and is more preferably based upon the molecular mass of, and/or the nucleotide sequence of, the fragment(s) obtained in the restriction step d), such as a mass spectroscopy technique, in particular of MALDI-TOF; and/or a chromatography technique, such as high pressure liquid chromatography (HPLC); or a suitable combination thereof, such as Gas Chromatography-Mass Spectroscopy (GC-MS).

16 Claims, 10 Drawing Sheets

1 2 3 4 5 6

METHOD FOR GENERATING OLIGONUCLEOTIDES, IN PARTICULAR FOR THE DETECTION OF AMPLIFIED RESTRICTION FRAGMENTS OBTAINED USING AFLP®

The present invention relates to a method for generating, and optionally detecting, oligonucleotides.

In particular, the present invention relates to a method for generating, from any desired starting DNA, DNA fragment or mixture of DNAs or DNA fragments, oligonucleotides of a known and predetermined length which are specific for said starting DNA(s) or DNA fragment(s) and which can suitably be detected using mass spectroscopy or a similar detection technique.

According a preferred embodiment, the method of the invention can be used to detect amplified restriction fragments obtained using AFLP® and/or to analyse a mixture of amplified restriction fragments obtained using AFLP®

Selective restriction fragment amplification or AFLP® is known, for instance from the European patent application 0 534 858 by applicant, incorporated herein by reference. In general, AFLP® comprises the steps of:

(A) digesting a nucleic acid, in particular a DNA, with one or more specific restriction endonucleases, to fragment said DNA into a corresponding series of restriction fragments;

(B) ligating the restriction fragments thus obtained with at least one doubled-stranded synthetic oligonucleotide adapter, one end of which is compatible with one or both of the ends of the restriction fragments, to thereby produce tagged restriction fragments of the starting DNA;

(C) contacting said tagged restriction fragments under hybridising conditions with at least one oligonucleotide primer;

(D) amplifying said tagged restriction fragments hybridised with said primers by PCR or a similar technique so as to cause further elongation of the hybridised primers along the restriction fragments of the starting DNA to which said primers hybridised; and (E) identifying or recovering the amplified or elongated DNA fragment thus obtained.

According to the prior art, the amplified DNA-fragments thus obtained can then be analysed and/or visualised, for instance by means of gel-electrophoresis. This provides a genetic fingerprint showing specific bands corresponding to the restriction fragments which have been linked to the adapter, have been recognised by the primer, and thus have been amplified during the amplification step. The fingerprint thus obtained provides information on the specific restriction site pattern of the starting DNA, and thus on the genetic make-up of the organism from which said DNA bas been derived.

AFLP® can therefore be used to identify said DNA; to analyse it for the presence of specific restriction site patterns, restriction fragment length polymorphism's (RFLP's) and/or specific genetic markers (so-called "AFLP-markers"), which may be indicative of the presence of certain genes or genetic traits; or for similar purposes, for instance by comparing the results obtained using DNA-samples of known origin or restriction pattern, or data thereon.

The primers used in AFLP® are such that they recognise the adapter and can serve as a starting point for the polymerase chain reaction. To this end, the primers must have a nucleotide sequence that can hybridise with (at least part of) the nucleotide sequence of the adapters(s) ligated to the end(s) of the restriction fragment to be amplified. The primers can also contain one or more further bases (called "selective bases") at the 3'-end of their sequence, for hybridisation with any complementary base or bases at the corresponding positions in the adapter ligated restriction fragment, i.e. adjacent to the adapter(s) and the restriction site(s). As, of all the adapter ligated restriction fragments present in the mixture, only those fragments that contain bases complementary to the selective bases will subsequently be amplified efficiently, the use of these "selective" primers will reduce the total amount of bands in the final fingerprint, thus making the fingerprint more clear and more specific. Also, the use of different selective primers will generally provide differing fingerprints, which can also be used as a tool for the purposes of identification or analysis.

As AFLP® provides amplification of both strands of a double stranded starting DNA, AFLP® advantageously allows for exponential amplification of the fragment, i.e. theoretically according to the series 2, 4, 8, 16, etc. Also, AFLP® requires no prior knowledge of the DNA sequence to be analysed, nor prior identification of suitable probes and/or the construction of a gene library from the starting DNA.

For a further description of AFLP®, its advantages, its embodiments, as well as the techniques, enzymes, adapters, primers and further compounds and tools used therein, reference is made to EP-0 534 858, incorporated herein by reference. Also, in the description hereinbelow, the definitions given in paragraph 5.1 of EP-0 534 858 will be used, unless indicated otherwise.

Although AFLP® is generally less time-consuming than other hybridisation-based techniques such as PCR-based detection, it still suffers from the disadvantage that the amplified fragments have to be separated (i.e. by (gel-) electrophoresis) and visualised (i.e. by generation of a fingerprint). These very elaborate and time-consuming procedures, which require special apparatus, such as electrophoresis and autoradiography equipment. Thereafter, the fingerprints have to be analysed—nowadays generally performed by "reading" the fingerprint into a computer—to identify the polymorphic bands. Generally, this also requires using a known reference sample run at the same time in a parallel lane of the gel.

Because of these factors, AFLP® can only be carried out in sufficiently equipped laboratories. Even so, it may take several days until results are obtained, even when routine tests following known protocols are carried out, such as on species or individuals of which the genome and/or relevant AFLP®-markers are generally known.

A first aim of the invention is to simplify these procedures, i.e. to provide a technique analysing nucleic acid sequences, which no longer requires the use of (gel-) electrophoresis and/or autoradiography.

The use of mass-spectroscopy techniques such as matrix assisted laser desorption/ionisation time-of-fight (MALDI-TOF) for detecting/identifying single strand DNA fragments is known, for instance from WO 97/47766; WO 99/54571; WO 99/02728; WO 97/33000, as well as Griffin et al., *Proc. Natl. Acad. Sci. USA.*, Vol. 96, pp. 6301–6306 (1999); Ross et al., Nature Biotechnology, Vol. 16 (1998), p. 1347–1351; and Berkenkamp et al., Science, Vol. 281 (1998), p. 260–262.

However, MALDI-TOF generally cannot be used to identify/detect the restriction fragments obtained using AFLP®, i.e. the fragments obtained in step (d) above. This is because MALI-TOF is limited to detection of single strand (hereinbelow further indicated as "ss") oligonucleotides with a length of at most 100, and preferably at most 30 bases, whereas the AFLP®-generated amplified fragments are mostly double stranded (hereinbelow indicated as "ds") DNA fragments which typically have a length in the range of 50–1200 base pairs.

Mass spectroscopy techniques have been used for the identification/detection of oligonucleotide sequences generated using PCR-amplification. In these methods, a starting DNA is amplified by a PCR using primers that are specifically designed to hybridise with the starting DNA at a site/sequence that is located in close proximity to a (single nucleotide) polymorphism (SNP) and that contain a recognition site for a restriction endonuclease of the IIS-type. Following the PCR, the amplified DNA is restricted with the corresponding IIS restriction endonuclease to generate small ds oligonucleotide fragments, which are converted to a corresponding ssDNA and detected using mass spectroscopy. Such a technique—using ESI-MS—is for instance described by Laken et al., Nature Biotechnology, vol. 16 (1998), p. 1352–1356.

However, these techniques suffer from the general disadvantage of PCR-based techniques, in that at least some prior knowledge of the sequence to be analysed is required, i.e. sufficient to provide a primer that can hybridise with the starting DNA.

By comparison, AFLP® requires no such prior knowledge of the sequence to be analysed. Thus, another objective of the invention is therefore to provide a method which combines the advantages of AFLP® with the ease and high throughput of detection that can be achieved using MALDI-TOF or a similar detection technique. This objective is achieved by the method(s) described hereinbelow.

In a first aspect, the invention relates to a method for generating, and optionally detecting, an oligonucleotide, comprising at least the steps of:
a) providing a first dsDNA;
b) ligating the first dsDNA to a second ds DNA, in which said second dsDNA sequence comprises within its sequence at least one (sequence corresponding to a) recognition site for an IIS restriction endonuclease; so as to provide a ligated dsDNA;
d) restricting the ligated dsDNA with the at least one restriction endonuclease of the IIS type so as to obtain at least a first and a second IIS-restricted dsDNA;

and optionally comprises the further step of:
e) detecting the first and/or the second IIS-restricted dsDNA obtained in the restriction step d).

Optionally, this method comprises the further step of:
c) amplifying the ligated ds DNA obtained in the ligating step b) prior to the restriction step d);

Further aspects, advantages and embodiments of the invention will become clear from the description given below.

Preferably, the detection step e) comprises the following steps:
e1) generating at least one ssDNA from either the first or the second IIS-restricted dsDNA obtained in the restriction step d);
e2) detecting the at least one ssDNA generated from either the first or the second IIS-restricted dsDNA.

The detection step e) preferably involves a detection method based upon the sequence and/or the molecular mass of the dsDNA obtained in the restriction step d). According to the preferred embodiment involving steps e1) and e2), the detection step e) involves a detection method based upon the molecular mass of the ssDNA generated in step e1).

In particular, mass spectroscopy techniques, and more in particular MALDI-TOF; and/or chromatography techniques, more in particular high pressure liquid chromatography (HPLC) may be used; or a suitable combination thereof.

In the Figures:
FIGS. 1 to 3 are schematic drawings illustrating the method of the invention for generating detectable oligonucleotides.

FIGS. 4 and 5 are DNA fingerprints obtained in Example 1 and Example 2, respectively.

FIG. 6 schematically shows an alternative method of the invention for generating detectable oligonucleotides using an IIS-type restriction endonuclease that is capable of restricting dsDNA at two sites different from the recognition site.

Figure 1:
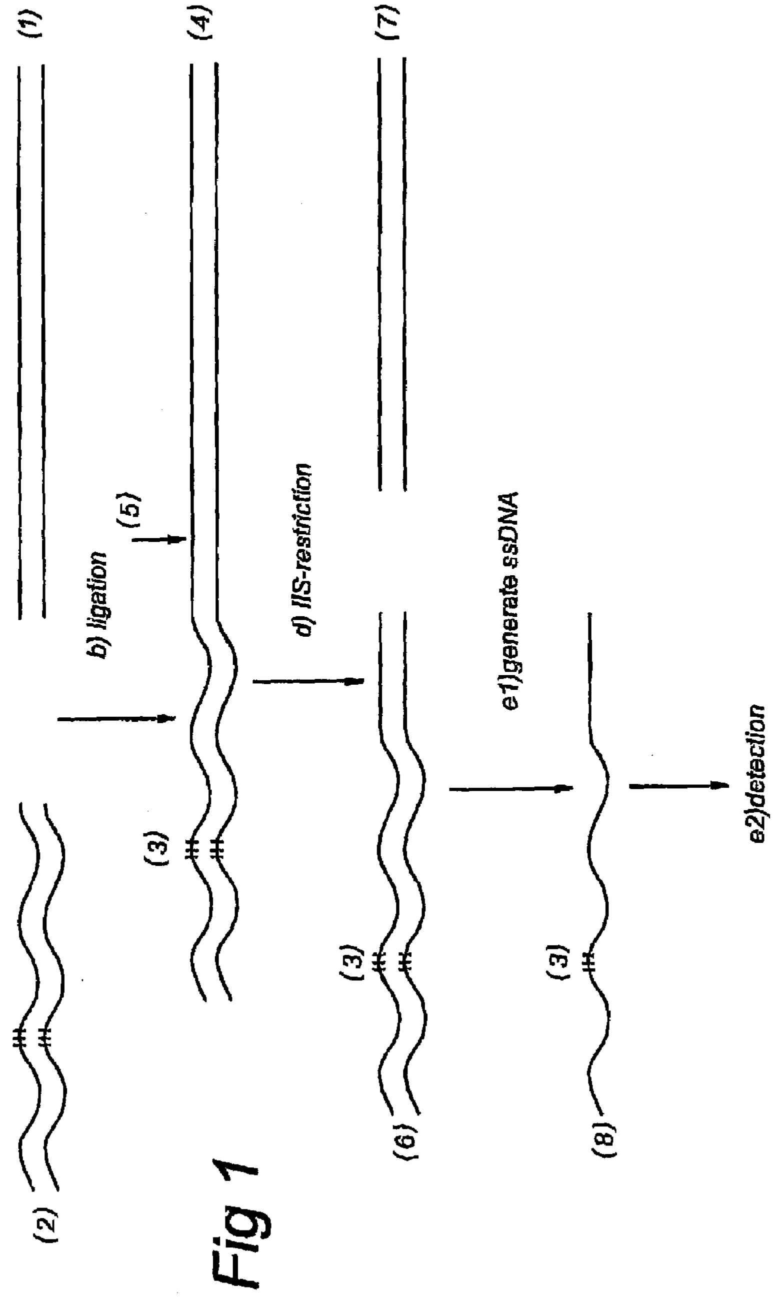

Usually, the first dsDNA will be a naturally occurring DNA or DNA fragment (including genomic DNA and/or a fragment thereof); a cDNA or a cDNA fragment; and/or an amplified DNA or DNA fragment (although preferably—as in step c) above—an amplification step forms part of the method of the invention). As such, the first dsDNA or dsDNA fragment may be part of a mixture of such dsDNAs or dsDNA fragments.

Preferably, as mentioned below, the first dsDNA is a restriction fragment. As such may be part of a mixture of restriction fragments obtained by restricting a starting DNA, and in particular a genomic DNA or cDNA, with one or more restriction enzymes.

Also, as further described below, when the starting dsDNA or dsDNA fragment is part of a mixture or sample containing several such dsDNAs or dsDNA fragments, it is possible, using the method of the invention, to generate—e.g. simultaneously and/or in a single reaction—oligonucleotides from (i.e. specific for) only one of the dsDNAs or dsDNA fragments present in the mixture or sample; from several of the dsDNAs or dsDNA fragments present in the mixture or sample; from a specific subset of the dsDNAs or dsDNA fragments present in the mixture or sample; or from essentially all of the dsDNAs or dsDNA fragments present in the mixture. In such a case, according to the invention, it may be possible to separately/independently detect (each of) the oligonucleotide(s) specific for each of the dsDNAs or dsDNA fragments present in the original mixture or sample.

Thus, the method of the invention may be used to analyse such a sample or mixture, for instance for determining the presence or absence of one or more specific dsDNAs and/or for distinguishing between one or more specific dsDNAs, in which the one or more dsDNAs may for instance be one or more restriction fragments corresponding to one or more genetic markers of interest.

The second dsDNA will comprise within its sequence at least a recognition site for an IIS restriction endonuclease. Herein, by an IIS (restriction) endonuclease is meant an endonuclease that restricts a dsDNA at a site/position on the dsDNA different from its recognition site, and in particular an endonuclease that restricts a dsDNA at a certain "distance" from the recognition site, usually from 5 to 30 base pairs, and preferably more than 15 base pairs, from the recognition site, in which said "distance" is defined as the number of base pairs situated between "last" base(pair) of the recognition site and "first" base pair of the restriction site.

Some non-limiting examples of type IIS endonucleases suitable for use in the invention and their recognition site(s) are mentioned in Table 1:

| Endonuclease | Recognition site |
|---|---|
| *Mme*I | 5' TCCRAC$(N)_{20}$ 3' (SEQ ID NO.41) 3' AGGYTG$(N)_{18}$ 5' (SEQ ID NO.42) |
| *Eco*57I | 5' CTGAAG$(N)_{16}$ 3' (SEQ ID NO.43) 3' GACTTC$(N)_{14}$ 5' (SEQ ID NO.44) |
| *Bsg*I | 5' GTGCAG$(N)_{16}$ 3' (SEQ ID NO.45) 3' CACGTC$(N)_{14}$ 5' (SEQ ID NO.46) |
| *Gsu*I | 5' CTGGAG$(N)_{16}$ 3' (SEQ ID NO.47) 3' GACCTC$(N)_{14}$ 5' (SEQ ID NO.48) |
| *Taq*II | 5' CACCCA$(N)_{11}$ 3' (SEQ ID NO.49) 3' GTGGGT$(N)_{9}$ 5' (SEQ ID NO.50) |
| *Tth*111II | 5' CAARCA$(N)_{11}$ 3' (SEQ ID NO.51) 3' GTTYGT$(N)_{9}$ 5' (SEQ ID NO.52) |
| *Bsm*FI | 5' GGGAC$(N)_{10}$ 3' (SEQ ID NO.53) 3' CCCTG$(N)_{14}$ 5' (SEQ ID NO.54) |
| *Fok*I | 5' GGATG$(N)_{9}$ 3' (SEQ ID NO.55) 3' CCTAC$(N)_{13}$ 5' (SEQ ID NO.56) |
| *Bbv*I | 5' GCAGC$(N)_{8}$ 3' (SEQ ID NO.57) 3' CGTCG$(N)_{12}$ 5' (SEQ ID NO.58) |

Other suitable IIS restriction enzymes will be clear to the skilled person and are for instance mentioned in U.S. Pat. No. 5,658,736 and WO 98/48047 and include e.g. AceIII, AlwI, AlwXI, Alw26I, BbvI, BbvII, BbsI, BccI, Bce83I, BcefI, BcgI, BinI, BsaI, BsgI, BsmAI, BsmF1, BspMI, EarI, EciI, Eco31I, Eco57I, Esp3I, FauI, FokI, GsuI, HgaI, HinGUII, HphI, Ksp632I, MboII, MmeI, MnlI, NgoVIII, PleI, RleAI, SapI, SfaNI, TaqII and Tth111II.

The second dsDNA will usually have a known and predetermined "size"/"length" (by which is meant the total number of base pairs/nucleotides thereof). Also, the position of the IIS recognition site in the second dsDNA will usually be known and pre-determined and will be such that, in the ligated DNA obtained in step b), the restriction site of the IIS endonuclease lies in the part of the ligated DNA that has been derived from/corresponds to the dsDNA. If so, the restriction step c), two IIS-restricted dsDNA fragments will be obtained, i.e. one containing the second dsDNA (with the IIS recognition site) and a part of the first dsDNA (i.e. that in the ligated dsDNA was directly adjacent to the second dsDNA); and one containing the remainder of the first dsDNA. Of these two IIS restricted fragments, for reasons that will be further explained hereinbelow, in step e) preferably the fragment comprising (a sequence corresponding to) the second dsDNA which includes the IIS recognition site is detected. More preferably, in step e1), the at least one ssDNA is preferably generated from the fragment comprising (a sequence corresponding to) the second dsDNA, which is subsequently detected.

Usually, the second dsDNA will have a size/length of up to 20–50 base pairs, and preferably between 10 base pairs and 40 base pairs. The second dsDNA will usually also have at least one "end" that allows it to be ligated to the first dsDNA—e.g. using conventional DNA ligation protocols—which will usually depend upon the end(s) present on the first dsDNA. Preferably, the IIS recognition site will be at a "distance" from the end of the second dsDNA that is to be ligated to the first dsDNA (by which is meant the number of base pairs/nucleotides between the IIS recognition site and the end of the second dsDNA) of up to 6–10 base pairs, and preferably between 0 and 6 base pairs, depending upon the IIS endonuclease to be used.

Usually, the second dsDNA will be a synthetic sequence, although the invention is not limited thereto. According to one preferred embodiment, the second dsDNA essentially corresponds to, and/or is used in a manner essentially analogous to, a conventional dsAFLP® adapter sequence.

Also, when the method of the invention comprises an amplification step c), this is preferably carried out using at least one primer that can hybridise with that part of the second dsDNA that allows extension of the primer along the ligated dsDNA. More preferably, this primer contains a IIS restriction site as close a possible to its 3' prime end, so as to yield—after restriction with the appropriate IIS restriction endonuclease—an IIS restricted dsDNA with as many as possible nucleotides derived from the first dsDNA.

Also, the primer is preferably such that it can also hybridise with 1–10 bases, preferably 1–4 bases, of the first dsDNA that, in the ligated dsDNA obtained in step b), are immediately adjacent to the sequence derived from the second dsDNA, so as to allow efficient amplification of only as subset of ligated dsDNA fragments when present in a mixture containing multiple such ligated dsDNA fragments).

However, the invention is not limited thereto, but generally comprises the use of any primer that allows for extension along the ligated dsDNA. For instance, the invention also encompasses the use of a primer that can hybridise with the sequence of the second dsDNA—i.e. as present in the ligated dsDNA used as the template for the extension reaction—such that, upon hybridisation, the 3'-end of the primer is still some bases removed from the restriction site (e.g. the sequence corresponding to the first dsDNA).

As further described below, such a primer will essentially correspond to an AFLP® primer and, in its preferred embodiment, to a selective AFLP®-primer. As with selective AFLP® primers, which "selective nucleotides"are used—i.e. the specific (sequence of) nucleotides present in the primer that are to hybridise with the bases/nucleotides derived from the first dsDNA—is not essential, as long as (at least a degree of) selective amplification is obtained, i.e. amplification of only a subset of all ligated dsDNA(s) present in the sample or mixture. However, as in conventional AFLP, the selective nucleotides are preferably predetermined.

The invention will now be explained in more detail with reference to the non-limiting FIG. 1, which schematically shows the method of the invention.

In step b), a first dsDNA (1) is ligated to a second dsDNA (2) containing an IIS recognition site (3). The ligated dsDNA (4) thus obtained is restricted in step c) with the appropriate IIS restriction endonuclease, which cuts the ligated dsDNA (4) at a restriction site (5) which lies in the part of the ligated dsDNA (4) that has been derived from the first dsDNA (1). The position of the restriction site (5) relative to recognition site (3)—i.e. the "distance" between sites—essentially will be determined by the IIS restriction endonuclease used.

Upon restriction, two IIS restricted dsDNA fragments will be obtained, indicated as (6) and (7) in FIG. 1. One of these fragments—indicated as (6) in FIG. 1—will comprise the original second dsDNA with the IIS restriction site and part of the first dsDNA, whereas the other fragment—indicated as (7) in FIG. 1—will comprise the remainder of the original first dsDNA.

It should be clear that the total "length"/"size" of fragment (6) will be determined by the length of the second dsDNA (2), the position of the IIS-recognition site (3) therein, and by the "distance" from the IIS recognition site (3) that the IIS restriction endonuclease restricts the ligated dsDNA (4), i.e. the position of site (5). Therefore, by using a second dsDNA (2) of known and pre-determined length and with a known and pre-determined position of the IIS recognition site (3), an IIS restricted dsDNA fragment (6) can be obtained of known and predetermined length, the mass of which—respective of similar fragments (6) generated with the same second dsDNA and using the same IIS restriction endonuclease—will essentially be determined by the nucleotides/bases from the first dsDNA (1) present in the IIS restricted fragment (6). Thus, the mass and/or the nucleotide sequence of the IIS restricted fragments (6) will be indicative of/characteristic for the first dsDNA (1).

Preferably, of the nucleotides/base pairs present in the IIS restricted dsDNA fragment(s) (6) thus obtained, at least 8 nucleotides/base pairs, more preferably at least 10 nucleotides base pairs, and most preferably up to the maximum number of base pairs/nucleotides that can be achieved with the restriction endonuclease used, are derived from the first dsDNA. This increases the difference(s) in mass between the different IIS restricted dsDNA fragment(s) (6) that have been generated from the starting DNA using the method of the invention, which improves resolution/sensitivity.

The IIS-restricted fragment (6) may then be detected, for instance by a detection method based upon (differences in) molecular weight/mass and/or nucleotide sequence. According to the preferred embodiment of the invention, this is carried out by generating—i.e. in step d)—at least one ssDNA fragment (8) from the IIS—restricted fragment (6), and detecting said ssDNA fragments (8) by mass spectroscopy or a similar technique, most preferably by MALDI-TOF. For this purpose, the length/size of the ssDNA fragment (8) generated from dsDNA fragment (6) should be such that the fragment is suitable for detection by MALDI-TOF, i.e. be within the general range of up to a maximum of 10–100 nucleotides, and preferably between 1 nucleotide and 40 nucleotides.

Conveniently, the size of the ssDNA fragments (8) obtained can be (and is) determined by appropriate selection of (the size/length of) the second dsDNA (2), i.e. such that the IIS restricted dsDNA fragment (8) has a size that—after separation of the strands—directly yields ssDNA fragments (8) of suitable length/size. However, it is not excluded that, as part of the steps by which the ssDNA fragment (8) is generated from the dsDNA fragment (6), the length/size of the ssDNA fragment (8) obtained is reduced further, i.e. compared to the length/size of the dsDNA fragment (6), for instance to afford an ssDNA fragment (8) of suitable length for detection by MALDI-TOF from a larger dsDNA fragment (6); provided that the ssDNA fragment (8) obtained is still specific/characteristic for the first dsDNA (1).

The fragment(s), and in particular the ssDNA fragment(s) (8), may then be detected using a mass spectroscopy technique, and in particular a mass spectroscopy technique suitable for the detection of nucleic acids.

Generally, such a technique will involve an ionisation step and a detection step. The ionisation step may for instance be carried out using electronspray ionisation (ESI) or matrix assisted laser desorption ionisation (MALDI). The detection step may for instance be carried out using ion trap (IT), time-of-flight (TOF), or quadrupole, or Fourier transform ion cyclotron resonance (FTICR). Any suitable combination of such an ionisation and such a detection technique may be used, of which ESI-quadrupole, ESI-FTICR and MALDI-TOF are the most commonly used. In the invention, the use of MALDI-TOF is particularly preferred.

The mass spectroscopy may be carried out according to known protocols, and the spectrum obtained may be analysed in a manner known per se.

For a further description of the above and other suitable mass spectroscopy techniques and their use in analysing nucleic acid sequences, reference is inter alia made to WO 97/47766; WO 99/02728; WO 97/33000.

One advantage of the method of the invention is that the use of mass spectroscopy labels—although not excluded from the scope of the invention—is not required.

However, with respect to the detection of the IIS restricted fragments obtained in step (d) above—i.e. of fragment (6) and/or (7) in FIG. 1—it should be noted that the above represents a non-limiting preferred embodiment, and that other ways of detecting/analysing the IIS restricted fragments are possible.

For instance, instead of generating a ssDNA (8) from the IIS-restricted dsDNA fragment (6), it may also be possible to detect dsDNA fragment (6) directly. Also, it may be possible to detect the IIS-restricted dsDNA fragment (7) and/or a ssDNA generated therefrom (not shown in FIG. 1).

Also, although the use of mass spectroscopy (MS) based detection techniques, and in particular of MALDI-TOF is preferred, it may be possible to use other detection techniques such as chromatography techniques such as HPLC or gas chromatography (GC) techniques; or a suitable combination of chromatography and mass spectroscopy techniques, such as GC MS.

The preferred techniques via which the ssDNA fragment(s) (8) can be obtained from the IIS restricted dsDNA fragment (6) will be further discussed hereinbelow.

The invention will now be further illustrated with reference to its preferred embodiment and application, i.e. the detection of restriction fragments, more specifically the combined amplification and detection of restriction fragments using AFLP® methodology. In this aspect, the first dsDNA (1) will be a restriction fragment, usually present in a mixture of restriction fragments, e.g. generated as described hereinbelow. The second dsDNA (2) containing the IIS restriction site will correspond to an AFLP® adapter, i.e. be designed such that it has an IIS recognition site in its sequence.

Also, in this aspect of the invention, the method of steps a) to e) above will usually also comprise an amplification step c). Conveniently, for the purposes of said amplification, use will be made of the AFLP® adapter containing the IIS recognition site, and of AFLP®-primers corresponding thereto. Thus, in the invention, the adapter is used both to provide a suitable IIS recognition site as well as to provide for amplification of the restriction fragments.

This has the advantage that the method of the invention can conveniently be carried out as a conventional AFLP®-reaction/amplification, i.e. essentially according to steps (A) to (D) of EP 0 534 958 mentioned above or according to another AFLP® protocol known per se, in which steps (A) to (D) will essentially correspond to steps a) to c) of the method of the invention. For this, the only adaptation required compared to conventional AFLP® methodology will be the use of an adapter containing an IIS restriction site, which can further be used in a manner per se for AFLP® adapters.

Thereafter, the detection of the amplified restriction fragments—step (E) of the method of EP 0 534 858—is carried out in accordance with the method of the invention described above, i.e. according to steps d) and e) above. In essence, this means that the amplified mixture of restriction fragments is treated with the suitable IIS restriction endonuclease, upon which—preferably—the amplified ds restriction fragments are converted into ss fragments, which can then be detected, e.g. using MALDI-TOF. Thus, steps d) and e) of the present invention will replace gel electrophoresis and autoradiography in conventional AFLP®.

Furthermore, as the AFLP® amplification itself can be carried out in a manner known per se, the present invention can incorporate and benefit from all advantages of AFLP®, as well as all the embodiments of AFLP®. For instance, as in conventional AFLP®, the amplification step c)—i.e. step (D) of EP 0 534 858—can be carried out using selective primers, in order to selectively amplify only a subset of all the restriction fragments present in the starting mixture, thereby to reduce the total number of amplified fragments obtained.

As to the detection of the amplified fragment(s), the invention may be used to specifically detect one or more (oligonucleotides corresponding to) restriction fragments, which will usually correspond to one or more AFLP® markers of interest, thus directly providing information on the presence or absence of said marker(s) in the starting mixture.

Alternatively, or at the same time, the invention may also be used to generate and detect a set of oligonucleotides corresponding to all restriction fragments that were (selectively) amplified from the original restriction fragment mixture, and thus to provide—for instance—a pattern of peaks in a mass spectrum corresponding to each of these oligonucleotides. Such a pattern would then provide/represent a kind of “fingerprint” for the starting mixture—i.e. comparable to a pattern of bands obtained through gelelectrophoresis—which could be analysed, processed further and/or stored/compiled to form a database, e.g. in a manner essentially as known for conventional genetic fingerprints.

Thus, in a further aspect, the invention relates to results and/or data obtainable by analysing a nucleic acid or mixture of nucleic acids via the method of the invention. These results or data may for instance be in the form of a graph, an image, a score, a set of numbers, a mass spectrum, a chromatogram, digital or analogue data, or in another suitable form; and may optionally be stored on a suitable data carrier, including paper, photographic film, computer disc of files, a database, etc. This data may be as directly obtained from the MS equipment used, or may have been processed further, e.g. using a suitable computer algorithm.

Therefore, according to this preferred aspect, the invention relates to a method for carrying out AFLP®, comprising steps (A) to (E) from EP 0 534 858 as mentioned above, in which the amplified fragments obtained in step (D) are identified in step (E) by a mass spectroscopy technique, in particular of MALDI-TOF; and/or a chromatography technique, such as high pressure liquid chromatography (HPLC); or a suitable combination thereof, such as Gas Chromatography-Mass Spectroscopy (GC-MS). Preferably, a mass spectroscopy technique is used, and more preferably MALDI-TOF.

In yet another preferred aspect, the invention relates to a method for carrying out AFLP®, comprising steps (A) to (E) from EP 0 534 858, in which the amplified fragments obtained in step (D) are identified in step (E) by at least generating at least one ssDNA from at least one of the amplified fragments followed by identification/detection of the ssDNA via a detection method based upon the length, size, mass of the ssDNA. According to this aspect, the ssDNA can be identified using a mass spectroscopy technique, in particular MALDI-TOF.

Alternatively, the ssDNA may be detected using another technique based upon the nucleotide sequence of the fragment(s) to be detected, as this may improve the resolution/resolving power. Such a sequence-based detection technique may (also) allow for a distinction to be made between oligonucleotides that have the same molecular mass (e.g. in that they contain the same number of each of the nucleotides A, T, G or C) but different sequences (e.g. in that the sequence of said nucleotides A,T,G and/or C is different, in particular in that part of the oligonucleotides that is derived from the first dsDNA).

Also, in another preferred aspect, the invention relates to the use of an adapter that contains at least one (sequence corresponding to a) recognition site for at least one restriction endonuclease of the IIS type in AFLP®; and/or to the use of a primer that contains at least one (sequence corresponding to a) recognition site for at least one restriction endonuclease of the IIS type in AFLP®.

Yet another preferred aspect relates to the use of mass spectroscopy, and in particular of MALDI-TOF, in the detection/identification of amplified restriction fragments generated using AFLP®.

Another preferred aspect relates to the use of a chromatography technique, such as high pressure liquid chromatography (HPLC); or a suitable combination of a chromatography technique and a mass spectroscopy technique, such as Gas Chromatography-Mass Spectroscopy (GC-MS), in the detection/identification of amplified restriction fragments generated AFLP®.

Preferably, in these aspects, the mass spectroscopy technique, the chromatography technique, or the combined chromatography/mass spectroscopy technique is applied to ssDNA fragments, generated from amplified dsDNA restriction fragments.

In this AFLP-based embodiment of the invention, the first dsDNA is a restriction fragment present in a mixture of restriction fragments, preferably obtained by restricting a starting DNA with at least one “frequent cutter” restriction enzyme and at least one “rare cutter” restriction enzyme, for which reference is inter alia made to EP-A-0 534 858 and EP-A-721 987, both incorporated herein by reference.

The fragments thus obtained are ligated to AFLP® adapters containing an IIS recognition site. For the remainder, these adapter will be essentially equivalent to, and used in the same way as, conventional AFLP® adapters. However, in order to provide eventually ssDNA fragments of a size most suitable for detection by MALDI-TOF, the adapters should have a length of preferably at most 40 base pairs.

Also, the IIS recognition site should be at a position that is at least within 10 base pairs of the end of the adapter that is attached to the restriction fragment, depending upon the IIS endonuclease used. As described above, this is to ensure that, when the amplified restriction fragments are restricted with the IIS endonuclease—i.e. in step d) of the invention—the site at which the amplified fragment is restricted lies that part of the amplified fragment that has been derived from the original restriction fragment.

Also, when the restriction fragments are generated with a frequent cutter and a rare cutter, the adapter with the IIS recognition site is preferably attached to the end of the restriction fragment generated by the frequent cutter, as generally, this will eventually result in a detectable ssDNA containing two more bases derived from the restriction fragment.

After ligation of the adapters, the mixture is amplified, i.e. using primers that can hybridise with (at least part of) the adapter sequence in such a way as to allow extension of the primer along the restriction fragment (template). As mentioned, these steps are essentially carried out according to known AFLP® protocols, for which reference is again made to—inter alia—EP-A-0 534 858, incorporated herein by reference.

Preferably, as is known from conventional AFLP® methodology, the amplification may comprise several amplification steps. Also, preferably at least one amplification step involves the use of selective AFLP® primers, such as +1 to +6 primers. For instance, a combination of a non-selective preamplification and a selective +2/+3 amplification may be used, with the lowest number of selective nucleotides preferably included in the primer with the recognition sequence of the IIS restriction endonuclease.

The amplified mixture of fragments thus obtained is then analysed in accordance with the present invention, i.e. according to steps d) and e) above. For this purpose, in a first step, the amplified mixture is restricted with the IIS endonuclease. This generally provides two types of IIS restricted fragments, i.e. fragments comprising the adapter and part of the original restriction fragment; and fragments comprising the remainder of the original restriction fragment (It should be noted that, as in AFLP® adapters are attached to both sides of a restriction fragment, the invention may provide—for each amplified fragment—two IIS restricted fragments containing an adapter—each derived from one end of the amplified fragment—and one IIS restricted fragment comprising the remainder of the original restriction fragment). For this purpose, the AFLP-adapters may contain recognition sites of the same or different IIS restriction endonucleases, and in case of different IIS recognition sites in the respective adapters, subsequent restriction with the corresponding type IIS restriction endonuclease(s) may be carried out separately of simultaneously.

The IIS-restricted fragments can then be detected. Preferably, as with the general method set out above, this is carried out according to steps e1) and e2), i.e. by generating at least one ssDNA fragment corresponding to at least one of the dsDNA IIS restricted fragments. Also, this ssDNA fragment is again preferably derived from the IIS restricted fragment(s) containing the adapter sequence. Some preferred, but non-limiting methods for detecting the IIS restricted fragments, and in particular for generating the ssDNA fragments from the IIS restricted amplified ds-fragments, will now be described hereinbelow.

Generally, detectable ssDNA fragments could be generated by separating the IIS restricted dsDNAs into ssDNA fragments, and then detecting all ssDNAs thus obtained, or only a subset thereof (for instance generated using a suitable separation step). However, such a method—although not excluded from the scope of the invention—would be cumbersome and time consuming, and might not provide the desired resolution.

Therefore, the ssDNA fragment to be detected is preferably generated by the use of an exonuclease, which is used to degrade all nucleic acid(s) present in the mixture obtained after IIS restriction, except the ssDNA strand that is eventually (to be) detected.

For this purpose, the ssDNA fragment to be detected must be resistant to degradation by the exonuclease used. This can be achieved by using, in the amplification step c), an exonuclease-resistant primer, which during the amplification reaction is incorporated into (one of) the amplified strand(s). In a further preferred embodiment, the exonuclease-resistant primer also contains a biotin label, allowing for easy purification and manipulation of the amplified fragments through its affinity for streptavidin, whereby the latter may be coupled to a solid support such as e.g. magnetic beads.

As the exonuclease, any exonuclease known per se can be used. Most preferably, a 5'→3' exonuclease is used, such as T7 gene 6 exonuclease and λ exonuclease. These exonucleases and their use in are well known in the art, for instance from WO 94/16090 and EP 0 744 470.

The primer used will be resistant to the exonuclease used. In case of—for instance—a T7 gene 6 exonuclease or a λ exonuclease, the primer will usually contain within its sequence one and preferably several nucleotide derivatives that make the primer resistant to the exonuclease. These may include, but are not limited to, nucleotide derivatives in which one or two of the non-bridging oxygen atoms from the phosphate moiety has/have been replaced by a sulphur containing group such as phosphorothioate group, by an alkyl group, by a nitrogen containing group such as an amine group, or by a selenium containing group. The use of phosphorothioate nucleotides is especially preferred. For a further description of such exonuclease resistant primers and their preparation, reference is again made to WO 94/16090 and EP 6 744 470.

In the amplification step c), these exonuclease resistant primers are further used as described above—i.e. in a manner known per se for AFLP®—upon which they are incorporated into the amplified ligated dsDNA obtained, making one strand thereof exonuclease-resistant. If several amplification steps are used, such as a non-selective preamplification followed by a selective amplification, the exonuclease-resistant primer should be used in the final amplification step.

The amplified dsDNA thus obtained is then restricted in step d) with the IIS restriction endonuclease, essentially as described above, to generate the first and second IIS restricted dsDNAs. From this IIS restricted mixture, in step e1), an ssDNA appropriate for detection by MALDI-TOF can then be generated treatment with the appropriate exonuclease, optionally after a suitable pre-treatment of the dsDNA known per se, such as heat-denaturation. (Such a pre-treatment is usually not required when T7 gene 6 exonuclease is used).

Figure 2:
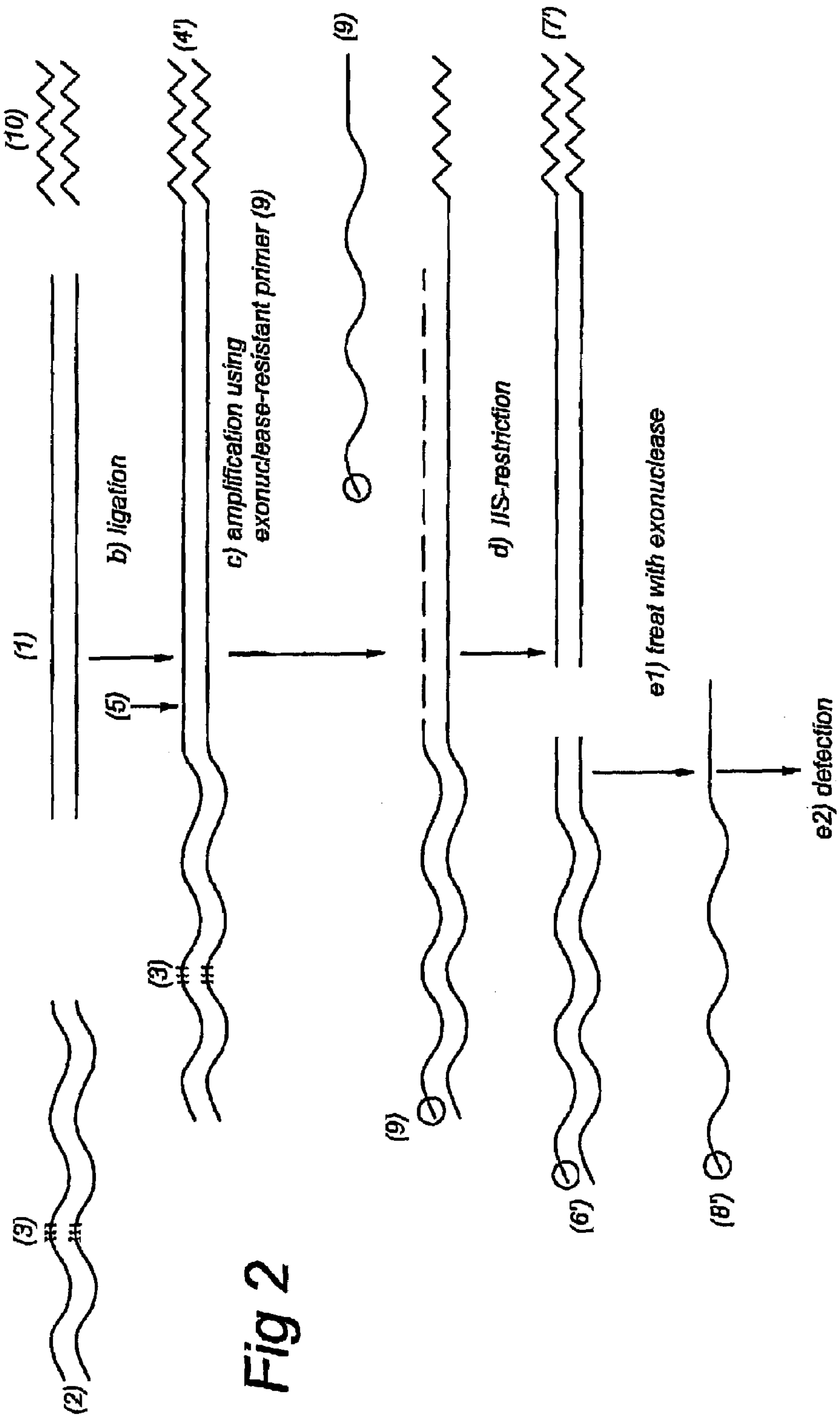

This aspect of the invention is schematically shown in FIG. 2, in which (9) represents the exonuclease-resistant primer and the other numerals are essentially as described for FIG. 1. As will be clear from the discussion of the preferred mode of the invention hereinabove, the first dsDNA (1) will usually be a restriction fragment obtained by restricting a starting DNA—e.g. genomic DNA or cDNA— with preferably) a frequent and a rare cutter; whereas the second dsDNA (2) will be an AFLP® adapter containing an IIS recognition site.

In the ligation step, the restriction fragment (1) is ligated to adapter (2), to provide a ligated dsDNA (4'). [Usually, a second AFLP® adapter—indicated as (10) in FIG. 2—will be ligated to the other end of fragment (1). This second adapter (10) may or may not (also) contain an IIS restriction site, as further discussed below.]

In step c), the ligated dsDNA (4) is then amplified, using a exonuclease resistant primer (9) that corresponds to adapter (2). [Besides the exonuclease resistant primer (9) usually also a second primer—not shown in FIG. 2—will be used that corresponds to adapter (10).]

After amplification, in step d), the amplified mixture is treated with the appropriate IIS restriction enzyme. As with step d) in FIG. 1, this will provide a first IIS restricted dsDNA (6') and a second IIS restricted dsDNA (7').

The first IIS restricted dsDNA (6') comprises the adapter (2) with the IIS recognition site (3) and part of (the sequence of) the original restriction fragment (1). Also, because of the presence of the exonuclease-resistant primer (9), one strand of the first IIS restricted dsDNA (6') is exonuclease-resistant. The second IIS restricted dsDNA (7') comprises the remaining part of the sequence of restriction fragment (1), as well as the second AFLP® (10), and is not resistant to degradation by an exonuclease [unless the second primer used is also exonuclease resistant, for instance as discussed below].

In step e1), the mixture from IIS restriction is treated with the exonuclease. This will remove all nucleic acids in the mixture that are not exonuclease-resistant, including the ssDNAs obtained from dsDNA (7'), the non-protected strand of dsDNA (6'), as well as (for example) remaining restriction fragments from the starting mixture that have not been amplified. This leaves the exonuclease resistant ssDNA (8'), which can then be detected.

Therefore, according to a preferred embodiment of the invention, in step c), an exonuclease-resistant primer is used, preferably an exonuclease resistant primer that corresponds to the second dsDNA of step b), i.e. the dsDNA containing the IIS recognition sequence. Also, according to this preferred embodiment, in step e1) a ssDNA is generated by treating at least (the strands of) the IIS restricted fragment that comprises (a sequence corresponding to) the second dsDNA of step b) with an exonuclease. Preferably, in step e1), the entire IIS restricted mixture obtained after step d) is treated with the exonuclease.

One further aspect of the invention therefore relates to the use in AFLP® of a primer that is resistant to an exonuclease, and in particular to a 5'→3' exonuclease, such as a T7 gene 6 exonuclease and/or a λ exonuclease. As will be clear from the above, the primer will usually also contain a sequence that corresponds to a recognition site of an IIS restriction endonuclease.

In another aspect, the invention relates to a kit for use with the above-mentioned method(s), said kit comprising (at least):

a restriction endonuclease of the IIS-type;

at least one dsDNA adapter containing at least one (sequence corresponding to a) recognition site for the restriction endonuclease of the IIS-type;

at least a primer adapted for use with said dsDNA adapter;

and optionally further components for kits for AFLP® known per se.

Said kit preferably also comprises an exonuclease, in particular a 5'→3' exonuclease, such as T7 gene 6 exonuclease and λ exonuclease, in which case at least one of the primers present in the kit will preferably be resistant to said exonuclease. The exonuclease resistant primer in the kit may preferably be a biotinylated primer, in which case the kit may further comprises streptavidin coupled to a solid support, such as e.g. magnetic beads.

It should be clear to the skilled person that variations and improvements on the above methodology are possible, without departing from the scope of the invention. These variations and improvements may for instance comprise the following:

The restriction fragment (1) may be ligated not to only one, but to two adapters containing an IIS recognition sequence, i.e. such that in FIG. 2, the "second" adapter (10) also contain an IIS recognition sequence (not shown in FIG. 2). This IIS recognition sequence in the second adapter (10) may be for the same IIS endonuclease, or for a different endonuclease, as the recognition sequence in the "first" adapter (2).

The method of the invention is further carried out in essentially the same manner as described above, albeit that—when the adapters (2) and (10) contain recognition sequences for different IIS endonucleases—the ligated dsDNA (4) is restricted in step d) with two IIS endonucleases, i.e. simultaneously, consecutively and/or independently. This will generate detectable fragments derived from both ends of the original restriction fragment (1)—i.e. comparable to fragments (6)/(6'), (7) or (8)/(8')—which are independent of each other and which may be detected separately or simultaneously, thus improving the reliability and/or the resolution of the invention. Also, detection of both ends of the fragment may provide for an internal reference/standard for the relevant marker during the MS detection, which may be of importance in the detection of certain important AFLP® markers. It will also be clear that in the embodiment of the invention where both ends of a restriction fragment (1) are detected, usually also two exonuclease resistant primers will be used for the amplification, each corresponding to one of the adapters (2) and (10) used.

Figure 3:
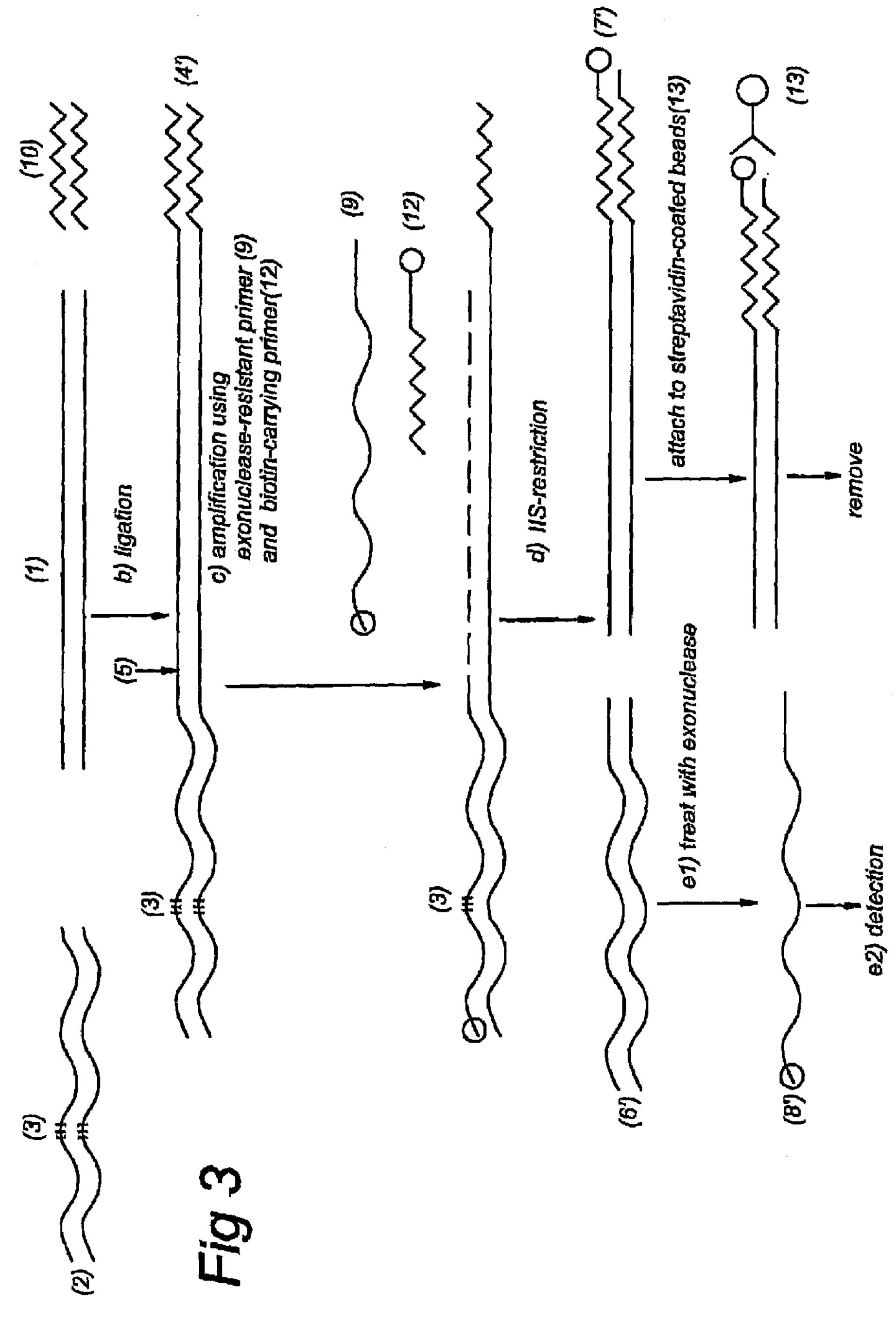

In the method of FIG. 2, the primer corresponding to the second adapter (10) may allow selective removal of the second IIS restricted dsDNA (7). This embodiment is schematically shown in FIG. 3, in which (11) is the primer corresponding to the second adapter (10). This primer (11) carries a functional group (12) that allows fragment (7) to be (selectively) removed, for instance a biotin group that allows the fragment(s) (7) to be selectively attached to streptavidin coated beads (13). After removal of the fragments (7), the first IIS restricted dsDNA (6) remaining in the supernatant may then be detected, as dsDNA or as a corresponding ssDNA. It will be clear to the skilled person that in this embodiment groups, ligands or binding pairs other than biotin/streptavidin may also be used.

Even more generally, the method of the invention comprises any method in which either the first IIS restricted dsDNA fragment(s) (6) or second IIS restricted dsDNA fragment(s) (7) are selectively removed or isolated from the IIS restriction mixture obtained after step d), upon which either the remaining and/or the removed fragment(s) may be detected.

Also, it may be possible to generate, from the first or second IIS restricted dsDNA obtained in step d), not one but two ssDNAs, i.e. one for/from each strand. In this embodiment, the two ssDNAs generated from the same IIS-restricted dsDNA may be of different length. For instance, the ssDNA corresponding to the complementary (i.e.

"antisense") strand may be 2 base pairs shorter than the ssDNA corresponding to the coding (i.e. "sense") strand, and may serve as an internal reference or standard, in particular for the detection of specific AFLP® markers.

Furthermore, when exonuclease-resistant primers based on phosphorothioate bonds are used, the position(s) of these bonds may be modulated and/or chosen such that the primers provide detectable ssDNA fragments that are optimised for the detection window of the mass spectroscopy technique used.

During the amplification step(s), mismatch amplification may be used/induced, which may cause the IIS recognition site to overlap with the restriction site for the rare or frequent cutter. In this way, the number of bases/nucleotides derived from the restriction fragment—which determine the differences in mass or sequence that is (to be) detected—may be increased, which may further improve the resolution that can be obtained.

Optionally, after the IIS restriction step d), the ds DNA fragments—e.g. dsDNA fragments (6) and/or (7)—may be further restricted with one or more further restriction endonucleases, such as a combination of several "4-cutters", to provide (a set of) specific, detectable fragments of different length (and thereby of different mass). This may increase the resolution and/or increase the number of "unique" detectable fragments obtained.

Also, according to a further embodiment of the invention, the IIS-restriction step d) may be replaced by restriction with one or more further restriction endonucleases, such as a combination of one or more "4-cutters". This may provide a set of restriction fragments, of which one, several or essentially all fragments may then be detected in a suitable manner, for instance based upon differences in mass, size, weight, or sequence of the fragment(s). Again, this may increase the resolution and/or increase the number of "unique" detectable fragments obtained.

As mentioned above, the method of the invention can be used to analyse a mixture of amplified restriction fragments generated using AFLP®. As such, the method of the invention can be used for all purposes that conventional AFLP® (i.e. involving gel electrophoresis/autoradiography) and/or variants or improvements thereof can be used.

For instance, the method of the invention can be used to analyse any kind of nucleic acid sequence or mixture of nucleic acid sequences, including, but not limited to, plant-derived sequences, animal-derived sequences, human-derived sequences, microbial sequences, yeast sequences, sequences from fungi and algae, viral sequences, as well as synthetic sequences.

For example, the method of the invention may be used to analyse DNA sequences, including genomic DNA, cDNA, structural genes, regulatory sequences and/or parts thereof; as well as RNA, including mRNA, optionally by analogous modification of the method given above. One particular application of interest could be the detection of cDNA-AFLP® fragments.

In these and other applications, the method of the invention can be used for any purpose for which a polymorphic marker or a transcribed gene sequence can be used and/or identified. This includes, but is not limited to, all the uses described in the art for polymorphic markers in known DNA-fingerprinting, genotyping, transcript profiling and DNA-identification techniques. The method of the invention is of course especially suited in these applications for which an AFLP®-marker can be used and/or identified, including those mentioned above and in EP-A-0 534 858 and the co-pending European applications 98.202.5496 and 98.202.4515. It is also envisaged that by the method of the invention, new genetic markers may be identified, and these form a further aspect of the invention.

For instance, the method of the invention may be used to classify an individual as belonging to a certain species, subspecies, variety, cultivar, race, strain or line, or to study the inheritance of a genetic trait or property. Also, the method of the invention may be used to detect markers indicative of the presence, the absence or the state of a genetically determined or genetically influenced disease or disorder, including cancer, oncogenes and oncogenic mutations, in which case the method of the invention may be used for diagnostic purposes.

Possible fields of use therefore include, but are not limited to, plant and animal breeding, variety or cultivar identification, diagnostic medicine, disease diagnosis in plants and animals, identification of genetically inherited diseases in humans, family relationship analysis, forensic science, organ-transplant, microbial and viral typing such as multiplex testing for strains of infectious diseases; as well as the study of genetic inheritance, gene expression, mutations, oncogenes and/or drug resistance; or for mRNA detection.

In particular, the method of the invention may be used for the high throughput detection of single nucleotide polymorphism's or SNPs. It is expected that on the basis of such SNPs, using association studies, important genes involved in diseases in humans and/or other organisms may be identified and/or studied. The high sensitivity of the method of the invention would make it possible to distinguish between SNP alleles.

Also, the method of the invention may be used to determine quantitatively the amount of a specific DNA, DNA-fragment or marker present in a starting sample. For instance, in transcript profiling using cDNA-AFLP®, the method of the invention may be used for the quantitative determination of the amount of cDNA in a biological sample. Also, the method of the invention may be used to provide quantitative data in homozygote/heterozygote-AFLP® techniques.

Besides the advantages already mentioned hereinabove, some further advantages of the method of the invention include:

as the method of the invention is based upon detection of the mass or the sequence of the fragments generated, there is no interference from cross-hybridisation effects, as may occur with hybridisation-based detection methods including array-based techniques.

the method of the invention may make it possible for specific markers to be determined or scored quantitatively, e.g. based on peak area and/or peak height.

the use of radioactive or fluorescent labels is not required (although a suitable use thereof is not excluded from the scope of the invention).

the use of mass labels is not required (although a suitable use thereof is not excluded from the scope of the invention).

in most of its embodiments, the invention only comprises enzymatic steps. These can be carried out in a single reaction vessel, and/or can easily be automated.

Contrary to gel-based detection techniques, AFLP®-markers of all sizes can be detected. These include fragments/markers of sizes that cannot be detected easily using current gel-electrophoresis techniques, e.g. fragments/markers of 600 base pairs or more.

the method of the invention can achieve high throughput. Also, results for a specific sample can be generated quickly.

In principle, the presence or absence of a single peak in the mass spectrum or chromatogram generated may already be indicative for the presence of absence of a marker or cDNA-AFLP fragment of interest.

Figure 6:
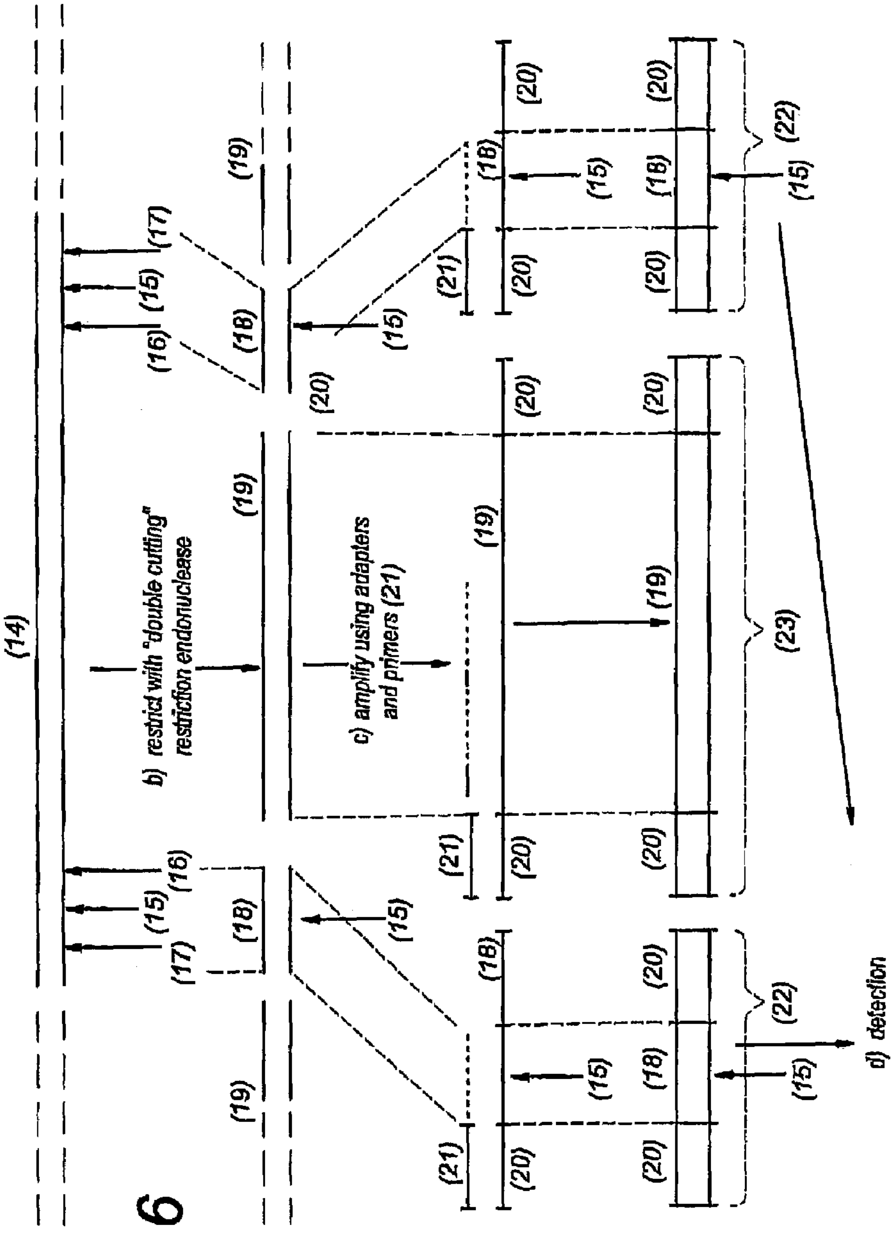

In another embodiment of the invention, schematically shown in FIG. 6, oligonucleotides suitable for detection using MALDI-TOF and/or one of the other techniques mentioned above are generated using a restriction endonuclease that is capable of restricting a starting nucleic acid (indicated as (14) in FIG. 6) at two sites, in particular at two sites different from the recognition site, and more in particular one site located upstream of the recognised sequence(s) and one site located downstream of the recognised sequence(s). (In FIG. 6, the recognition site is indicated as (15) and the two restricted sites (are indicated as (16) and (17), respectively).

Some non-limiting examples of such "double cutting" restriction endonucleases are: BaeI, which has the recognition sequence:

BaeI, which has the recognition sequence:

N N N N N^N N N N N N N N N N N A C N N N N G T A Y

C N N N N N N N N N N N N N
(SEQ ID NO.59)

N N N N N N N N N N N N N N N N T G N N N N C A T R G
N N N

N N N N^N N N N N
(SEQ ID NO.60)

BcgI, which has the recognition sequence:

N N^N N N N N N N N N N N C G A N N N N N N T G C N

N N N N N N N N N N N
(SEQ ID NO.61)

^N N N N N N N N N N N N G C T N N N N N N A C G N
N N

N N N N N N N^N N
(SEQ ID NO.62)

BplI, which has the recognition sequence:

N N N N N^N N N N N N N N G A G N N N N N C T C N

N N N N N N N N N N N N
(SEQ ID NO.63)

^N N N N N N N N N N N N N C T C N N N N N G A G N
N N N

N N N N^N N N N N
(SEQ ID NO.64)

Bsp24I, which has the recognition sequence:

N N N N N^N N N N N N N N G A C N N N N N N T G G

N N N N N N N N N N N N
(SEQ ID NO.65)

^N N N N N N N N N N N N N C T G N N N N N N A C C
N N

N N N N N^N N N N N
(SEQ ID NO.66)

CjeI, which has the recognition sequence:

N N N N N N^N N N N N N N N C C A N N N N N N G T

N N N N N N N N N N N N N N N
(SEQ ID NO.67)

^N N N N N N N N N N N N N N G G T N N N N N N C A
N

N N N N N N N N^N N N N N N
(SEQ ID NO.68)

CjePI, which has the recognition sequence:

N N N N N N^N N N N N N C C A N N N N N N N T C N

N N N N N N N N N N N N N
(SEQ ID NO.69)

^N N N N N N N N N N N N G G T N N N N N N N A G N
N N

N N N N N^N N N N N N
(SEQ ID NO.70)

and AloI and Hin4I, of which BcgI is preferred, due to the fact that only two base overhangs are created, which improved the specificity of ligating the second dsDNA to the first dsDNA.

Thus, by restricting a starting nucleic acid, such as a dsDNA, in particular a genomic DNA or a cDNA, with such a "double cutting" restriction endonuclease, it is possible to generate one or more fragments of between 20–50, usually between 30–40 b.p., and often 34 or 36 bp in length/size. These fragments, which are indicated as (18) in FIG. 6, usually will contain the recognition site/sequence(s) (10) of the restriction endonuclease used, as well as about 30 (depending on the restriction endonuclease used) "unknown" bases which are fully dependant upon the starting nucleic acid used. Thus, besides having a size suitable for detecting by MALDI-TOF and/or one of the other techniques mentioned above, these fragments are also specific/representative for the starting nucleic acid (14).

Usually, when a plant-derived DNA is used as the starting nucleic acid (14), such "double cutting" restriction endonucleases will cut said DNA with a frequency of about once per 3000 base pairs. Thus, this generally provides a mixture of the "small" restriction fragments (18) mentioned above and "large" restriction fragments. These large fragments, which are indicated as (19) in FIG. 6, will usually have a size of several hundreds or even thousands of base pairs, and on average about 2000 to 3000 base pairs, and usually will not contain a sequence corresponding to the recognition site/sequence(s) of the restriction endonuclease used.

In principle, it could be possible to specifically detect one or more—or essentially all—of the fragments(18) and/or (19) present in the thus restricted mixture, and in particular to detect one or more—or essentially all—of the small fragments (18), optionally after isolating said fragment(s) (18) from the restricted mixture and/or selectively removing the large fragments (19).

According to the invention, however, the restricted mixture is most preferably first amplified, even more preferably using at least one selective amplification step in order to reduce the complexity of the fragment mixture. Then, according to this preferred method, one or more—or essentially all—of the amplified fragments (18) and /or (19), and in particular one or more of the amplified small fragments (18), are detected, e.g. using MALDI-TOF and/or one of the other detection techniques mentioned above.

Said amplification is most preferably carried out using known AFLP® methodology, i.e. by ligating the fragments present in the restricted mixture—i.e. both the small fragments (18) as well as the large fragments (19)—to at least one adapter and then amplifying the mixtures using primers suitable for use with said adapters. (In FIG. 6, the adapters are indicated as (20) and the primers are indicated as (21). This can be carried out essentially a described hereinabove and in—inter alia—EP-A-0 534 858, incorporated herein by reference.

Also, said amplification may comprise a single amplification step or several amplification steps. As already mentioned, in order to reduce the complexity of the mixture, in (at least one of) the amplification step(s), a primer containing at least one selective nucleotide is used, as is known from AFLP® methodology. For instance, a combination of a non-selective preamplification and one or more selective amplifications may be used, or a combination of several selective amplification steps, each using primers with an increasing number of selective nucleotides, e.g. as described in Example III below. Preferably, in order to avoid mismatches, in an amplification comprising several amplification steps, the number of selective nucleotides is not increased by more than 1 or 2 selective nucleotides for each round of amplification.

Also, in the amplification preferably a mixture of at least two adapters is used, more preferably adapters with differing adapter-core sequences (not shown FIG. 6). With these adapters, most preferably also a mixture of at least two primers suitable for use with these said adapters are used (also not shown in FIG. 6).

Also, preferably, the amplification conditions are chosen such that the adapter-ligated "small" fragments (18) are amplified more efficiently then the adapter-ligated "large" fragments (19), e.g. by using a amplification profile (e.g. time, temperature) that is sufficient to allow for full elongation of the primer(s) (21) along the adapter-ligated short fragments (18) but that is insufficient for full elongation of the primers(s) (21) along the adapter-ligated large fragments (19).

After the amplification, an amplified mixture is obtained that for the major part consists of the amplified adapter-ligated "small" fragments (indicated as (22) in FIG. 6) and the amplified adapter-ligated "large" fragments (indicated as (23) in FIG. 6). This amplified mixture can then be analysed in a manner known per se, i.e. by (specifically) detecting one or more—or essentially all—of the amplified adapter-ligated "small" fragments (22), one or more—or essentially all—of the amplified adapter-ligated "large" fragments (23), or a combination thereof, optionally, after removing the adapter sequences by digestion with the "double cutting" restriction enzyme to improve the resolution of detection.

Preferably, one or more—or essentially all—of the amplified adapter-ligated "small" fragments (22) are detected, e.g. using mass spectroscopy such as MALDI-TOF, and/or one of the other techniques mentioned above, such as a chromatography technique; or a suitable combination thereof. For this purpose, the length of the adapters (20)/primers (21) used in the amplification step(s) is preferably chosen such that the amplified adapter-ligated "small" fragments (22) obtained are still of a size suitable for such detection, e.g. as mentioned above. When conventional AFLP-adapters and -primers are used, e.g. of about 10–30 base pairs in length, this will usually be the case, e.g. provide amplified adapter-ligated "small" fragments (22) of between 50 and 100 bp, preferably between 60 ad 80 bp, and usually about 70 bp.

Again, as in the methods described above, the one or more adapter-ligated small fragments (22) may be detected as double stranded fragments (e.g. as directly obtained after amplification), or as single stranded sequences generated from the amplified double stranded fragments (22) (not shown in FIG. 6).

Before detection, the one or more adapter-ligated small fragments (22) to be detected may be (specifically) isolated from the amplified mixture. For instance, the one or more adapter-ligated small fragments (22) may be separated from the adapter-ligated "large" fragment(s) (23) and/or any other fragments/components present in the amplified mixture, or the adapter-ligated "large" fragment(s) (23) may be (selectively) removed from the amplified mixture.

This may be carried out in any suitable manner, for instance using a suitable separation technique, such as a technique based on the difference(s) in size between the small fragments (22) and the large fragments (23). Alternatively, primers (22) may be used in the amplification that allow for (selective) isolation of the amplified fragments. For instance, in the final amplification step, a primer (21) may be used that carries a biotin group, which allows the amplified fragments to be selectively isolated using a streptavidin-coated carrier, such as streptavidin coated magnetic beads (not shown in FIG. 6).

Also, optionally, in the (final) amplification (step), a set of primers may be used that each have different mass. This would allow analysis of different primer combinations simultaneously without overlap between the masses of the different fragments/oligonucleotides.

This aspect of the invention generally provides the same advantages as already mentioned above. In particular, a short time is required for detection, which allows for high throughput. Also, there is no need to use autoradiography and/or radioactive/fluorescent labels, and oligonucleotides are obtained that are specific for the starting nucleic acid and that can be analysed using a detection technique based on (differences in) the mass.

Furthermore, compared to the method described above, this aspect of the invention offers the following further advantages:

A higher proportion—i.e. essentially all in case of digestion of the amplified ligated restriction fragments with the "double cutting RE"—of the nucleotides in the amplified (small) fragments (18) that are eventually detected—e.g. as amplified fragments (22)—will be derived from the starting nucleic acid (14). These generally include the nucleotides that correspond to the recognition sequence (17) of the "double cutting" restriction endonuclease used, as well as the about 30 "unknown" nucleotides present in the small fragments (18). This not only means the differences in mass between the individual oligonucleotides (22) to be detected are increased, but also that the chances that different fragments (18)/(22) will have the same mass (but for instance only a different nucleotide sequence) will be reduced, e.g. to 3% or less. This improves sensitivity and/or resolution.

The primers used in the amplification will be independent of the restriction enzyme used.

Thus, this aspect of the invention relates to a method for generating, and optionally detecting, an oligonucleotide, comprising at least the steps of:

a) providing a dsDNA;
b) restricting the dsDNA with at least one restriction endonuclease that restricts the dsDNA at two sites different from the recognition site of said restriction endonuclease, so as to provide a mixture of restricted fragmented, said mixture comprising one or more fragments that contain the recognition site/sequence(s) of the restriction endonuclease and one or more fragments that do not contain a sequence corresponding to the recognition site/sequence(s) of the restriction endonuclease used; and
d) detecting at least one of the restricted fragments obtained in step b).

In step (d), preferably one or more—or essentially all—of the fragments that contain the recognition site/sequence(s) of the restriction endonuclease are detected, optionally after (specific) isolation of these (one or more) fragments from the mixture obtained in step b).

Preferably, this method comprises the steps of:
a) providing a dsDNA;
b) restricting the dsDNA with at least one restriction endonuclease that restricts the dsDNA at two sites different from the recognition site of said restriction endonuclease, so as to provide a mixture of restricted fragments, said mixture comprising one or more fragments that contain the recognition site/sequence(s) of the restriction endonuclease and one or more fragments that do not contain a sequence corresponding to the recognition site/sequence(s) of the restriction endonuclease used;
c) amplifying the mixture of fragments obtained in step b);
d) detecting at least one of the amplified fragments obtained in step c), or, optionally, after digesting the amplified fragments with the "double cutting RE" to remove the adapter sequences.

In step (d), preferably one or more—or essentially all—of the amplified fragments that contain the recognition site/sequence(s) of the restriction endonuclease are detected, optionally after specific isolation of these (one or more) fragments from the amplified mixture obtained in step c). Preferably, the primer(s) used in the amplification in step (c) are biotinylated, such that the fragments from the amplified mixture may be isolated using streptavidin on a solid support such as e.g. magnetic beads.

The amplification of step c) is preferably carried out using AFLP® methodology, e.g. as described above. The detection of step d) is preferably carried out using mass spectroscopy such as MALDI-TOF, or a chromatography technique, such as high pressure liquid chromatography (HPLC); or a suitable combination of a chromatography technique and a mass spectroscopy technique, such as Gas Chromatography-Mass Spectroscopy (GC-MS).

For further preferences and embodiments of this aspect of the invention, reference is made to the general description above.

The invention will now be illustrated by means of the following non-limiting Experimental Part.

Experimental Part

EXAMPLE I

AFLP fingerprints produced with AFLP adapters and selective amplification primers, which contain a recognition site for type IIS restriction enzymes GsuI or BsgI.

AFLP fingerprints generated with the standard AFLP adapters- and selective amplification primers, which do not contain a type IIS site, are included as controls.

1. Biological Material

The biological materials used are the parental lines of a population of recombinant inbred lines of *Arabidopsis*. These parental lines are the ecotypes Colombia (sample No. NW20) and Landsberg erecta (sample nr. N933) and were acquired from the arabidopsis stock centre in Nottingham (UK).

2. EcoRI/MseI AFLP Template Preparation, Preamplification and Selective Amplification.

All procedures were conducted according to the standard protocols (Vos et al., Nucleic Acids Research 23: no 21, pp. 4407–4414, and patent application EP0534858). AFLP reactions were labelled radioactively with $^{33}$P and resolved on a standard AFLP (sequence) gel. The sequences of the adapters, preamplification primers and selective amplification primers are as follows:

2.1 Standard AFLP Procedure (FIG. 4, Lanes 1 and 2):

```
EcoRI adapter:
91M35:  5'-ctcgtagactgcgtacc-3'  and   (SEQ ID NO.1)
91M36:  3'-catctgacgcatggttaa-5'       (SEQ ID NO.2)

EcoRI + 1 preamplication primer:
E01K:   5'-gactgcgtaccaattca-3'        (SEQ ID NO.3)

EcoRI + 2 selective amplification primer:
E12:    5'-gacctgcgtaccaattcac-3'      (SEQ ID NO.4)

MseI adapter:
92A18:  5'-gacgatgagtcctgag-3'         (SEQ ID NO.5)
92A19:  3'-tactcaggactcat-5'           (SEQ ID NO.6)

MseI + 1 preamplification primer:
M02:    5'-gatgagtcctgagtaac-3'        (SEQ ID NO.7)

MseI + 3 selective amplification primer:
M47:    5'-gatgagtcctgagtaacaa-3'      (SEQ ID NO.8)
```

Figure 4:
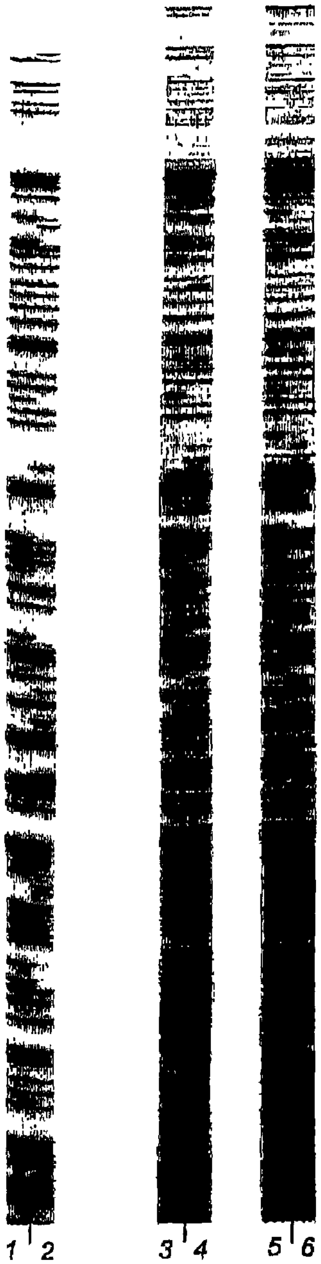

2.2 AFLP Fingerprints Generated with MseI Adapter- and AFLP Primers Containing a GsuI Site (5'-3' CTGGAG $N_{16}/N_{14}$)(SEQ ID NO.71). (FIG. 4 Lanes 3 and 4).

EcoRI adapter, preamplification AFLP primer and selective AFLP primer: for sequences see 2.1.

```
MseI adapter:
99I21: 5'-gacgatgagtctggag-3'          (SEQ ID NO.9)
99I22: 5' tactccagactcat-3'            (SEQ ID NO.10)

MseI + 1 preamplication primer:
99I23: 5'-gacgatgagtctggagtaac-3'      (SEQ ID NO.11)

MseI + 3 selective amplification primer:
99I25: 5'-gacGATGAgtctggagtaacaa-3'    (SEQ ID NO.12)
```

(nucleotides shown in uppercase are joined by phosphorothioate bonds to confer resistance to T7 gene 6 exonuclease).

2.3 AFLP Fingerprints Generated with MseI Adapter- and AFLP Primers Containing a BsgI Site (5'-3' GTGCAG $N_{16}/N_{14}$)(SEQ ID NO.15). (FIG. 4 Lanes 5 and 6).

EcoRI adapter, preamplification AFLP primer and selective AFLP primer: for sequences see 2.1.

```
MseI adapter:
99I37:  5'-gacgatgagtgtgcag-3'         (SEQ ID NO.13)
99I38:  5'-tactgcacactcat-3'           (SEQ ID NO.14)

MseI + 1 preamplification primer:
99I40:  5'-tactgcacactcat-3'           (SEQ ID NO.14))
```

MseI+3 selective amplification primer:

99I41: 5'-gacGATCAgtgtgcagtaacaa-3' (SEQ ID NO.16)

(nucleotides shown in uppercase are joined by phosphorothioate bonds to confer resistance to T7 gene 6 exonuclease).

3. Result

FIG. 4 shows that very similar fingerprints are obtained when the standard AFLP adapters and primers are used (lanes 1 and 2) or when AFLP adapters and primers are used which contain a GsuI site (lanes 3 and 4) or a BsgI type IIS site (lanes 5 and 6).

Lanes 1, 3 and 5 contain the EcoRI/MseI +2/+3 fingerprints derived from sample N933.

Lanes 2, 4 and 6 contain the EcoRI/MseI +2/+3 fingerprints derived from sample NW20.

(the +2/+3 selective nucleotides are the same in all cases (lanes 1–6) and correspond to EcoRI primers E12 (+AC) and MseI primer M47 (+CAA).

Lanes 7 contains a 10 basepair ladder a size reference.

EXAMPLE II

Restriction Enzyme Digestion of AFLP Reactions Generated with an MseI AFLP Adapter and Amplification Primer Containing a Type IIS Restriction Enzyme Site.

1. Biological Material

The biological material used are two recombinant inbred lines (RIL) of Arabidopsis (samples numbers 1923 and 1904). The parental lines are of the RIL population are the ecotypes Colombia and Landsberg erecta. The RIL were acquired from the arabidopsis stock centre in Nottingham (UK).

2. EcoRI/MseI AFLP Template Preparation, Preamplification and Selective Amplification.

All procedures were conducted according to the standard protocols (Vos et al., Nucleic Acids Research 23: no 21, pp. 4407–4414, and patent application EP0534858. The sequences of the adapters, preamplification primers and selective amplification primers are as described in Example I with the exception of:

2.1 Standard AFLP Amplification:

Selective amplification primer M47 was substituted for primer

MS50: 5'-gatgagtcctgagtaacat-3 (SEQ ID NO.17)

2.2 AFLP Fingerprints Generated with MseI Adapter- and AFLP Primers Containing a GsuI Site.

+3 MseI selective amplification primer I25 was substituted for primer I32: 5'-gacgATGAGtctggagtaacag-3' (SEQ ID NO.18)

(nucleotides shown in uppercase are joined by phosphorothioate bonds to confer resistance to Exonuclease T7 gene 6).

2.3 AFLP Fingerprints Generated with MseI Adapter- and AFLP Primers Containing a BsgI Site.

+3 MseI selective amplification primer I41 was substituted for primer I48: 5'-gacgATGAGtgtgcagtaacat-3' (SEQ ID NO.19)

(nucleotides shown in lowercase are joined by phosphorothioate bonds to confer resistance to T7 gene 6 exonuclease).

3. Preparing AFLP Reactions with Double Stranded Fragments.

After the selective amplification reaction according to the standard procedure in a 20 microliter volume with primers sequences are described in sections 2.1, 2.2 and 2.3, an identical amount of 20 microliter selective amplification reagents was added to yield a 40 microliter total volume, and an extra cycle of PCR amplification was conducted according to the thermal cycle profile 30 sec 94° C., 30 sec 56° C. and 4 min 72° C., to convert all AFLP fragments to double stranded DNA.

4. Restriction Enzyme Digestion.

Following the preparation of double stranded AFLP reactions as described in sections 2 and 3 above, a 5 microliter sample was taken from each tube as control prior to restriction enzyme digestion. To the remainder of each tube (35 microliter volume), 15 microliter restriction ligation buffer was added to yield a 50 microliter total volume, and 5 microliters GSuI or BsgI restriction enzyme was added to AFLP reactions prepared with the corresponding AFLP adapter- and primer sequences. The samples were incubated for 110 minutes at 37° C. (BsgI) or 30° C. (GsuI). After restriction enzyme digestion another 5 microliter aliquot was taken, mixed with loading dye, and loaded along with the undigested control samples on a 18% polyacrylamide gel.

5. Results

FIG. 5 contains:

AFLP reactions prepared with GsuI site containing MseI adapter- and AFLP primers:

Lane 1: sample 1923, AFLP reaction E12/I32 (GsuI site) before restriction enzyme digestion.

Lane 2: sample 1904, AFLP reaction E12/I32 (GsuI site) before restriction enzyme digestion.

Lane 3: sample 1923, AFLP reaction E12/I32 (GsuI site) after restriction enzyme digestion.

Lane 4: sample 1904, AFLP reaction E12/I32 (GsuI site) after restriction enzyme digestion.

AFLP reactions prepared with BsgI site containing MseI adapter- and AFLP primers:

Lane 5: sample 1923, AFLP reaction E12/I48 (BsgI site) before restriction enzyme digestion.

Lane 6: sample 1904, AFLP reaction E12/I48 (BsgI site) before restriction enzyme digestion.

Lane 7: sample 1923, AFLP reaction E12/I48 (BsgI site) after restriction enzyme digestion.

Lane 8: sample 1904, AFLP reaction E12/I48 (BsgI site) after restriction enzyme digestion.

Standard AFLP reactions

Lane 9: sample 1923, standard AFLP reaction E12/M50 before restriction enzyme digestion.

Lane 10: sample 1904, standard AFLP reaction E12/M50 before restriction enzyme digestion.

Lane 11: sample 1923, standard AFLP reaction E12/M50 after restriction enzyme digestion.

Lane 12: sample 1904, standard AFLP reaction E12/M50 after restriction enzyme digestion.

Size ladder

Lane 13: contains a 10 basepair size ladder as a reference for fragment size.

FIG. 5 shows:

1) A strong fragment of 32 bases in lanes 3 and 4 as expected after digestion with GsuI.

2) A strong fragment of 32 bases in lanes 7 and 8 as expected after digestion with BsgI.

3) No restriction fragment of 32 bases in the remaining lanes (samples prior to digestion with GsuI or BsgI or any of lanes 9–12 which contain the standard AFLP reactions).

Figure 5:
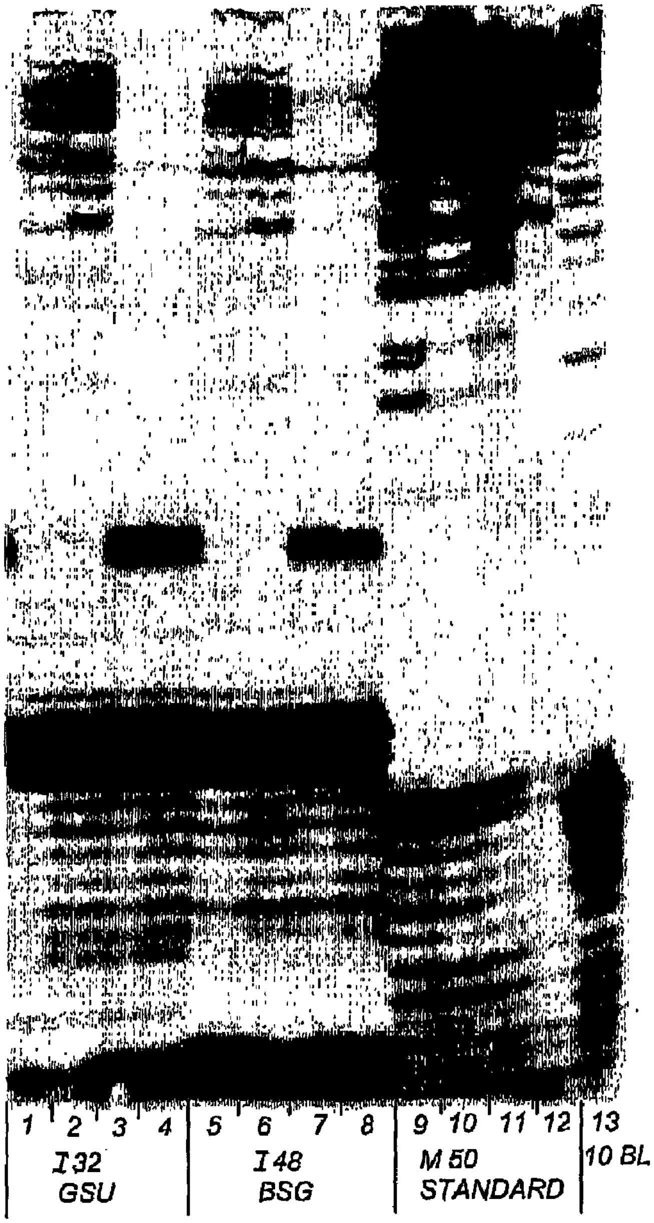

In conclusion FIG. 5 shows that double stranded AFLP oligotags can be generated by preparation of AFLP templates with adapters and AFLP primers containing a BsgI or GsuI site, and digestion of AFLP reactions containing double stranded DNA fragments with these enzymes.

EXAMPLE III

Generating Specific Detectable Oligonucleotides Using a "Double Cutting" Restriction Endonuclease.

Genomic DNA is digested using BcgI, to provide a mixture that contains small fragments with the BcgI recognition sequence(s), as well as large fragments that do not contain any BcgI recognition site. The fragments containing BcgI recognition site can be schematically represented as follows:

```
5' nnnnnnnnnnCGAnnnnnnTGCnnnnnnnnnnnn-3'
(SEQ ID NO. 72)

3' nnnnnnnnnnnnGCTnnnnnnAGCnnnnnnnnnn-5'
(SEQ ID NO. 73)
```

The mixture of fragments is ligated to two different adapters (adapters X: xxxxxNN, adapter Y: yyyyyNN), each with a different core sequence, and amplified. The bottom strand will not ligate, but will be "filled in" during the first amplification step. This provides fragments having on their respective termini the adapters X-X, X-Y, Y-X or Y-Y.

```
x x x x x NN nnnnnnnnnnCGAnnnnnnTGCnnnnnnnnnn n n
(SEQ ID NO. 74)

YYYYYXXXXX n n nnnnnnnnnnGCTnnnnnnACGnnnnnnnnnn N

N y y y y y
(SEQ ID NO. 75)
```

The complexity of the mixture is reduced through amplification with primers containing selective nucleotides. To prevent mismatching, amplifications are carried out in which the number of selective nucleotides used in each amplification step is not increased by more than 1 or 2 per amplification step. Only the fragments with different adapters on both termini will amplify exponentially. Optionally, for a final +ATG/+CGA extension 2 or 3 consecutive amplifications are carried out. In the final amplification step, one primer will be labelled with a biotin-molecule ("bio").

```
bio- x x x x xATGnnnnnnnnnCGAnnnnnnTCGnnnnnnnnnTCG
(SEQ ID NO. 76)

YYYYYXXXXXTACnnnnnnnnnGCTnnnnnnACGnnnnnnnnnACG y y

y y y
(SEQ ID NO. 77)
```

The fragments are purified using streptavidin beads and the oligonucleotide-tags are isolated by treatment of the beads with alkali or by heat denaturation. The tags are obtained in the supernatant of the alkali or heat treatment.

XXXXXTACnnnnnnnnnGCTnnnnnnACGnnnnnnnnnAGCYYYYY(SEQ ID NO. 78)

The oligonucleotide tags are analysed using mass spectroscopy, e.g. by determining the mass of the tags with a length of 70 nucleotides, optionally, after digestion with BcgI to remove the non-informative adapter sequences, which results in a higher resolution to detect the resulting tags with a length of 32 nucleotides.

This method may be carried out as follows;

DNA-template is prepared by digesting 200–500 ng genomic DNA with 5 units of BcgI. The restriction fragments thus obtained are ligated to a mixture of the following adapters:

```
Adapter 1:  (SEQ ID NO.20 and 21)
5' CTCGTAGACTGCGTACCNN 3'

3' GAGCATCTGACGCATGG 5'

Adapter 2:  (SEQ ID NO.22 and 23)
5' GACGATGAGTCCTGAGANN 3'

3' CTGCTACTCAGGACTCT 5'
```

The mixture of adapter-ligated fragments is then amplified using a pre-amplification with a set of +1 and +2 primers for use with adapter 1 and adapter 2, respectively i.e.:

```
+1 primer for Adapter 1:
CTCGTAGACTGCGTACCN         (SEQ ID NO.24)

+2 primer for Adapter 2:
GACGATGAGTCCTGAGACN        (SEQ ID NO.25)
```

The preamplification profile comprises a short denaturation (1 sec, 94° C.) followed by a short elongation (5 sec., 56° C.), both repeated 40 times. Such a profile favours amplification of the adapter-ligated small fragments compared to amplification of the adapter-ligated large fragments.

The +1/+2 preamplification is followed by a selective +2 amplification, selective +3 amplification, or a selective +4 amplification (or a combination of +2, +3, or +4 selective amplifications) using the following primers:

```
+2 primer for Adapter 1:
CTCGTAGACTGCGTACCNN        (SEQ ID NO.26)

+3 primer for Adapter 2:
GACGATGAGTCCTGAGACNN       (SEQ ID NO.27)

+3 primer for Adapter 1:
CTCGTAGACTGCGTACCNNN       (SEQ ID NO.28)

+4 primer for Adapter 2:
GACGATGAGTCCTGAGACNNN      (SEQ ID NO.29)
```

One of the primers used in the final amplification step contains a 5'-biotin group. The mixture of amplified fragments is then isolated and purified by contacting the mixture with streptavidin coated magnetic beads. The oligonucleotide fragments are isolated by incubation of the beads carrying the restriction fragments with alkali or by heating (5 min. 95° C.). The supernatant thus obtained, containing the amplified restriction fragments, may then be analysed, e.g. using a mass spectroscopy technique such as MALDI-TOF. The selective amplification profile comprises a short denaturation (1 sec. 94° C.), followed by a short elongation (5 sec. 65° C.), both repeated 13 times, in which the elongation temperature is gradually lowered to 56° C. by a decrease of 0.7° C. per cycle, followed by another 23 cycles consisting of a denaturation step of 1 sec. at 94° C. and an elongation step of 5 sec. at 56° C.

EXAMPLE IV

Generation of Oligotags from AFLP Reactions Generated with a MseI AFLP Adapter and an Amplification Primer Containing a Type IIS Restriction Enzyme Site.

1. Biological Material

The biological material used are the two parental lines (samples IR20 and 6383) from a F2 population of Rice. The parental lines were acquired from the IRRI in the Philippines.

2. EcoRI/MseI AFLP Template Preparation, Preamplification and Selective Amplification.

Figure 7:
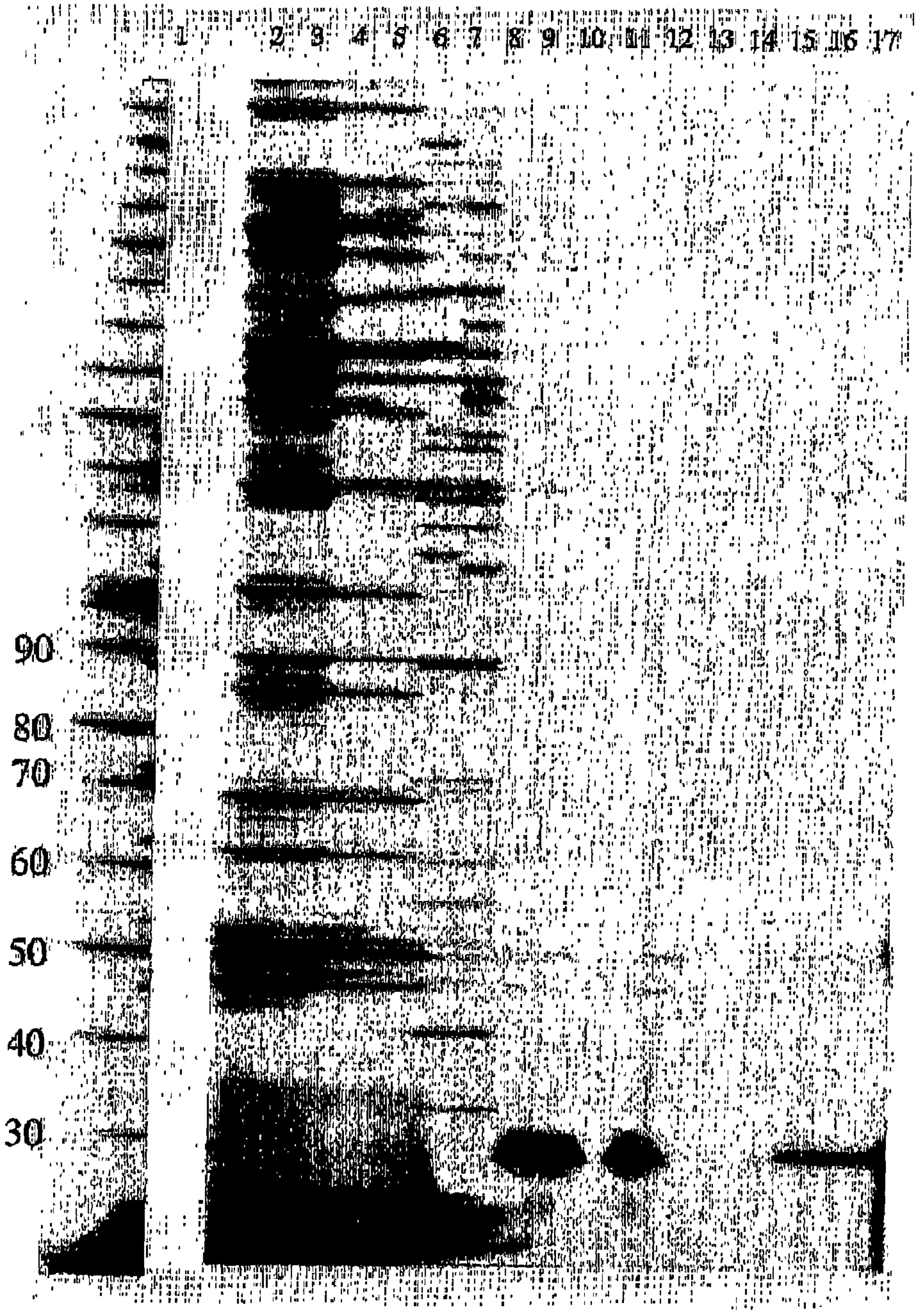
FIG. 7 shows AFLP reactions prepared with a MseI adapter- and AFLP primers containing a GsuI site.

All procedures were conducted according to the standard protocols (Vos et al., Nucleic Acids Research 23: no 21, pp. 4407–4414 and patent application EP0534858). AFLP reactions were radioactively labelled with 33P and resolved on a standard AFLP (sequence gel). The sequences of the adapters, preamplification primers and selective amplification primers are as described in Example I with the exception of:

2.1 AFLP Fingerprints Generated with MseI Adapter- and AFLP Primers Containing a GsuI Site (5'-3' CTGGAG N16/N14) (SEQ ID NO.79). (FIG. 7).

+3 MseI selective amplification primer I25 was substituted for primer 00s45thio: 5'-gatgaGTCTGGAGTAACAC-3' (SEQ ID NO.30), (nucleotides shown in lowercase are joined by phosphorothioate bonds to confer resistance to T7 gene 6 Exonuclease).

Figure 8:
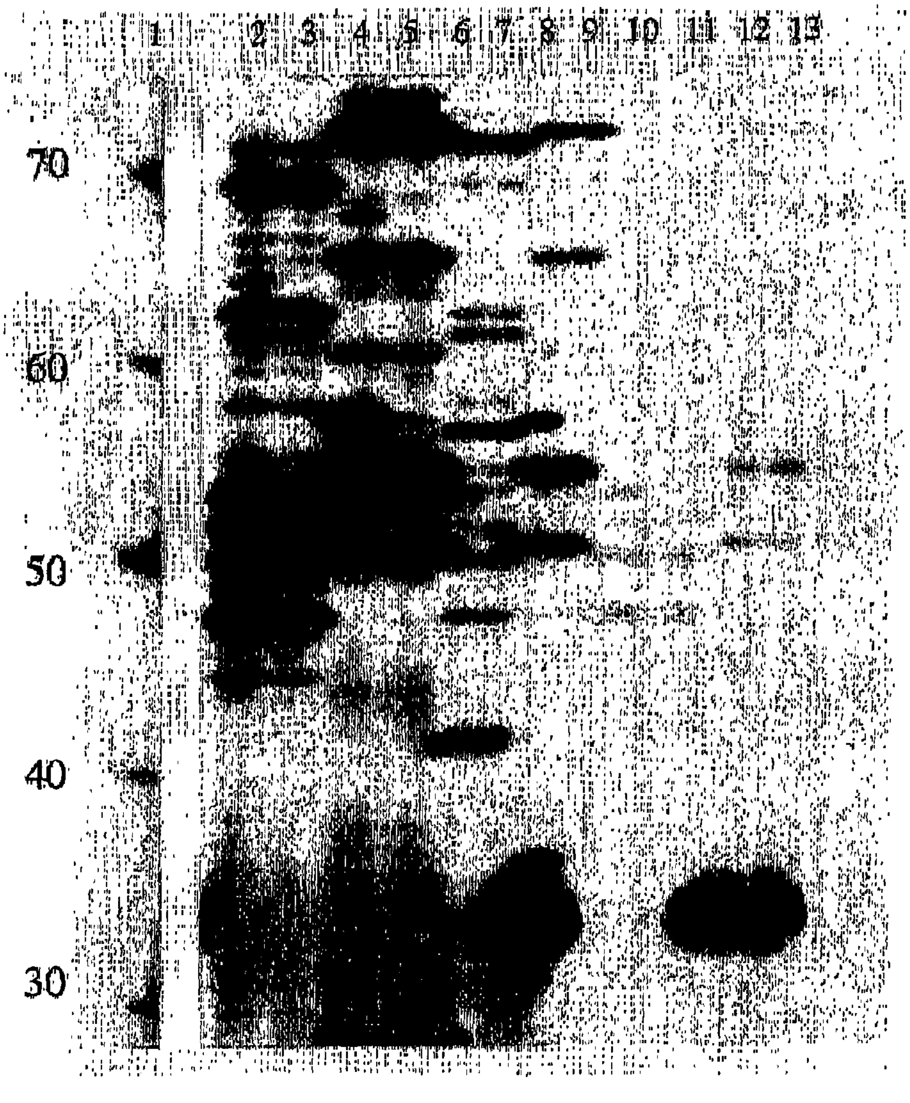
FIG. 8 shows AFLP reactions prepared with a MseI adapter- and AFLP primers containing a BsgI site.

2.2 AFLP Fingerprints Generated with MseI Adapter- and AFLP Primers Containing a BsgI Site. (5'-3' GTGCAG N16/N14) (SEQ ID NO.80). (FIG. 8).

+3 MseI selective amplification primer I41 was substituted for primer 00s24bio: 5'-GA(bioT)GAGTGTGCAG-TAACAC-3' (SEQ ID NO.31), (bioT refers to a biotin molecule coupled to the deoxythymidinenucleoside).

3. Preparing AFLP Reactions with Double Stranded Fragments.

After the selective amplification reaction according to the standard procedure in a 20 microliter volume with primer sequences described in sections 2.1 and 2.2, an identical amount of 20 microliter selective amplification reagents was added to yield a 40 microliter total volume, and an extra cycle of PCR amplification was conducted according to the thermal cycle profile 30 sec 94° C., 1 min 56° C. and 2 min 72° C., into convert all AFLP fragments to double stranded DNA.

4. Preparation of AFLP Oligonucleotide Tags.

Following the preparation of double stranded AFLP reactions as described in sections 2 and 3 above, a 10 microliter sample was taken from each tube and mixed with 10 microliter loading dye as a control prior to AFLP oligonucleotide tag preparation. To 10 microliter of each tube a 5 microliter mixture containing 0.5 microliter of 10× PCR buffer, 0.66 units ExonucleaseI, 0.594 microliter 10× Shrimp Alkaline Phosphatase buffer and ddH2O, was added to yield a 15 microliter total volume. The samples were incubated for 30 minutes at 37° C. followed by incubation for 10 minutes at 70° C. to inactivate the Exonuclease I. To this 15 microliter sample, 10 microliter restriction enzyme mix was added containing 2.5 microliter restriction enzyme buffer, 3 units of GsuI or BsgI restriction enzyme and S-adenosylmethionine according to the manufacturers specifications. The samples were incubated for 180 minutes at 30° C. (GsuI) or 37° C. (BsgI). After the restriction enzyme digestion a 5 microliter aliquot was taken, mixed with loading dye, and loaded on a sequence gel along with the untreated control sample, as a control for the digestion by the restriction enzymes.

The remainder of the restriction enzyme digestion mix was used to isolate the oligonucleotide tags.

To the GsuI digestion mix 5 microliter 5× T7 Gene 6 Exonuclease buffer and 5 units T7 Gene 6 Exonuclease was added and incubated for 1 hour at 37° C. followed by a 10 minutes incubation at 70° C. A 5 microliter sample was taken and mixed with 5 microliter loading dye and loaded on a sequence gel along with the earlier mentioned samples. The remainder of the sample was purified using a nucleotide removal kit from Qiagen.

The sample was eluted from the Qiagen column with 100 microliter ddH2O and concentrated by evaporation of water to an end volume of 15 microliter. This 15 microliter sample was mixed with 15 microliter loading dye and loaded on sequence gel together with the earlier mentioned samples.

To the BsgI digestion mix a mixture containing 5 microliter magnetic streptavidin coated beads reconstituted 80 microliter STEX solution (1000 mM NaCl/10 mM Tris HCl/1 mM EDTA/0.1% Triton X-100 pH 8.0), was added and incubated for 30 minutes at room temperature with gentle agitation. After this incubation the beads were concentrated with the magnetic particle concentrator and washed sequentially twice with 100 microliter STEX and once with 100 microliter ddH2O and reconstituted in 15 microliter. The oligonucleotide tags were incubated for 5 minutes at 95° C. and after concentration on a magnetic particle concentrator the supernatant was quickly removed and transferred to another sample tube and 15 microliter loading dye was added. This sample was loaded on a sequence gel together with the earlier mentioned samples.

All above mentioned samples were analysed on a denaturing 6% polyacrylamide gel.

5. Result

FIG. 7 contains:

AFLP reactions prepared with a MseI adapter- and AFLP primers containing a GsuI site:

Lane 1: contains a 10 basepair size ladder as a reference for fragment size; fragment sizes in basepairs are indicated on the left.

Lane 2: sample IR20, AFLP reaction E35/00s45thio (GsuI site) in which the E35 primer was labelled with 33P.

Lane 3: sample 6383, AFLP reaction E35/00s45thio (GsuI site) in which the E35 was labelled with 33P.

Lane 4: sample IR20, AFLP reaction E35/00s45thio (GsuI site) in which the 00s45thioprimer was labelled with 33P.

Lane 5: sample 6383, AFLP reaction E35/00s45thio (GsuI site) in which the 00s45thioprimer was labelled with 33P.

Lane 6: sample IR20, AFLP reaction E35/00s45thio (GsuI site) in which the E35 primer was labelled with 33P, followed by digestion with Exonuclease I and GsuI.

Lane 7: sample 6383, AFLP reaction E35/00s45thio (GsuI site) in which the E35 primer was labelled with 33P, followed by digestion with Exonuclease I and GsuI.

Lane 8: sample IR20, AFLP reaction E35/00s45thio (GsuI site) in which the 00s45thioprimer was labelled with 33P, followed by digestion with Exonuclease I and GsuI.

Lane 9: sample 6383, AFLP reaction E35/00s45thio (GsuI site) in which the 00s45thioprimer was labelled with 33P, followed by digestion with Exonuclease I and GsuI.

Lane 10: sample IR20, AFLP reaction E35/00s45thio (GsuI site) in which the E35 primer was labelled with 33P, followed by digestion with Exonuclease I, GsuI and T7 Gene 6 Exonuclease.

Lane 11: sample 6383, AFLP reaction E35/00s45thio (GsuI site) in which the E35 primer was labelled with 33P, followed by digestion with Exonuclease I, GsuI and T7 Gene 6 Exonuclease.

Lane 12: sample IR20, AFLP reaction E35/00s45thio (GsuI site) in which the 00s45thioprimer was labelled with 33P, followed by digestion with Exonuclease I, GsuI and T7 Gene 6 Exonuclease.

Lane 13: sample 6383, AFLP reaction E35/00s45thio (GsuI site) in which the 00s45thio primer was labelled with 33P, followed by digestion with Exonuclease I, GsuI and T7 Gene 6 Exonuclease.

Lane 14: sample IR20, AFLP reaction E35/00s45thio (GsuI site) in which the E35 primer was labelled with 33P, followed by digestion with Exonuclease I, GsuI and T7 Gene 6 Exonuclease and then followed by purification using a nucleotide removal column.

Lane 15: sample 6383, AFLP reaction E35/00s45thio (GsuI site) in which the E35 primer was labelled with 33P, followed by digestion with Exonuclease I, GsuI and T7 Gene 6 Exonuclease and then followed by purification using a nucleotide removal column.

Lane 16: sample IR20, AFLP reaction E35/00s45thio (GsuI site) in which the 00s45thioprimer was labelled with 33P, followed by digestion with Exonuclease I, GsuI and T7 Gene 6 Exonuclease and then followed by purification using a nucleotide removal column.

Lane 17: sample 6383, AFLP reaction E35/00s45thio (GsuI site) in which the 00s45thioprimer was labelled with 33P, followed by digestion with Exonuclease I, GsuI and T7 Gene 6 Exonuclease and then followed by purification using a nucleotide removal column.

FIG. 8 contains:

AFLP reactions prepared with a MseI adapter- and AFLP primers containing a BsgI site:

Lane 1: contains a 10 basepair ladder as a reference for fragment size; fragment sizes in basepairs are indicated on the left.

Lane 2: sample IR20, AFLP reaction E35/00s24bio (BsgI site) in which the E35 primer was labelled with 33P.

Lane 3: sample 6383, AFLP reaction E35/00s24bio (BsgI site) in which the E35 primer was labelled with 33P.

Lane 4: sample IR20, AFLP reaction E35/00s24bio (BsgI site) in which the 00s24bio primer was labelled with 33P.

Lane 5: sample 6383, AFLP reaction E35/00s24bio (BsgI site) in which the 00s24bio primer was labelled with 33P.

Lane 6: sample IR20, AFLP reaction E35/00s24bio (BsgI site) in which the E35 primer was labelled with 33P, after digestion with Exonuclease I and BsgI.

Lane 7: sample 6383, AFLP reaction E35/00s24bio (BsgI site) in which the E35 primer was labelled with 33P, after digestion with Exonuclease I and BsgI.

Lane 8: sample IR20, AFLP reaction E35/00s24bio (BsgI site) in which the 00s24bio primer was labelled with 33P, after digestion with Exonuclease I and BsgI.

Lane 9: sample 6383, AFLP reaction E35/00s24bio (BsgI site) in which the 00s24bio primer was labelled with 33P, after digestion with Exonuclease I and BsgI.

Lane 10: sample IR20, AFLP reaction E35/00s24bio (BsgI site) in which the E35 primer was labelled with 33P, after digestion with Exonuclease I and BsgI, followed by isolation of the oligonucleotide tags using magnetic streptavidin beads.

Lane 11: sample 6383, AFLP reaction E35/00s24bio (BsgI site) in which the E35 primer was labelled with 33P, after digestion with Exonuclease I and BcgI digested DNA I, followed by isolation of the oligonucleotide tags using magnetic streptavidin beads.

Lane 12: sample IR20, AFLP reaction E35/00s24bio (BcgI digested DNA I site) in which the 00s24bio primer was labelled with 33P, after digestion with Exonuclease I and BsgI, followed by isolation of the oligonucleotide tags using magnetic streptavidin beads.

Lane 13: sample 6383, AFLP reaction E35/00s24bio (BsgI site) in which the 00s24bioprimer was labelled with 33P, after digestion with Exonuclease I and BsgI, followed by isolation of the oligonucleotide tags using magnetic streptavidin beads.

FIG. 7 shows:

1) Labelling of either E35 or 00s24thio results in a comparable fingerprint as expected in lanes 2 and 4, and lanes 3 and 5 with some mobility changes due too sequence differences between the 33P labelled strands of the fragments.

2) Fragment sizes in lanes 6 and 7 are reduced by 29 nucleotides after digestion with GsuI compared to the fragment sizes in lanes 2 and 3.

3) As expected almost all fragments are digested by GsuI resulting in a strong fragment of 29 nucleotides in lanes 8 and 9.

4) Lanes 10 and 11 show that the by GsuI digested fragments seen in lanes 6 and 7 are as expected digested by T7 Gene 6 Exonuclease.

5) The 33P labelled 00s24thio containing fragments are as expected unaffected by the digestion of T7 Gene 6 Exonuclease as seen in lanes 12 and 13.

6) After purification with the nucleotide removal kit the fragments of 29 nucleotides are still present as seen in lanes 16 and 17.

FIG. 8 shows:

1) Labelling of either E35 or 00s24bio results in a comparable fingerprint as expected in lanes 2 and 4, and lanes 3 and 5 with some mobility changes due too sequential differences between the 33P labelled strands of the fragments and the presence of a biotin molecule (which results in a lower mobility of the fragments).

2) Fragment sizes in lanes 6 and 7 are reduced with 29 nucleotides after digestion with BsgI compared when with the fragment sizes in lanes 2 and 3.

3) As expected almost all fragments are digested by BsgI resulting in a strong fragment of 29 nucleotides (which due to the presence of a biotin molecule migrates as a fragment with a mobility of 34 nucleotides) in lanes 8 and 9.

4) After purification by the streptavidin coated magnetic beads the fragments of 29 nucleotides are still present in lanes 12 and 13.

EXAMPLE V

Generation of Oligotags by AFLP Reactions Using a Type IIS Restriction Enzyme, Adapter and Amplification Primer.

1. Biological Material

The biological material used are the two parental lines (samples IR20 and 6383) from a F2 population of Rice. The parental lines were acquired from the IRRI in the Philippines.

2. BcgI AFLP Template Preparation, Preamplification and Selective Amplification.

2.1 Template Preparation Using BcgI.

Template preparations were conducted according to the standard protocols (Vos et al., Nucleic Acids Research 23: no 21, pp. 4407–4414, and patent application EP0534858) with the exception that the BcgI restriction enzyme was inactivated by incubating the restriction digestion mix for 10 minutes at 70° C. prior to the ligation of the adapters. The sequences of the adapters, preamplification primers and selective amplification primers are as follows:

BcgI adapter sequence1:

```
00s25:  5'-ctcgtagactgcgtaccNN-3'    (SEQ ID NO.32)

00s26:  5'-ggtacgcagtctacgag-3'      (SEQ ID NO.33)
```

With N being any of the four deoxynucleosides A, C, G or T

BcgI adapter sequence2:

```
00s27:  5'-gacgatgagtcctgagaNN-3'    (SEQ ID NO.34)

00s28:  5'-tctcaggactcatcgtc-3'      (SEQ ID NO.35)
```

With N being any of the four deoxynucleosides A, C, G or T

```
BcgI + 1 preamplification primer on adapter
sequence 1:
00s29:
5'-ctcgtagactgcgtacca-3'            (SEQ ID NO.36)

BcgI + 2 preamplification primer on adapter
sequence 2:
00s35:
5'-gacgatgagtcctgagacc-3'           (SEQ ID NO.37)

BcgI + 3 amplification primer on adapter
sequence 1:
00s31bio:
5'-bio-ctcgtagactgcgtaccaca-3'      (SEQ ID NO.38)
```

(bio refers to a biotin molecule coupled to the 5'-end of the primer)

BcgI +4 amplification primers on adapter sequence 2:

```
00s41: 5'-gacgatgagtcctgagaccac-3'   (SEQ ID NO.39)

00s42: 5'-gacgatgagtcctgagaccag-3'   (SEQ ID NO.40)
```

2.2 Preamplifications.

Preamplification reactions were set up according to the standard protocols with the exception that the above mentioned primers (00s29 and 00s35) were used and that the thermal cycling protocol was adapted for amplification of small fragments.

The thermal cycling protocol used was 40 cycles with 1 sec 94° C. and 5 sec 56° C.

2.3 AFLP Selective Amplification.

AFLP reactions were radioactively labelled with 33P and resolved on a standard AFLP (sequence) gel.

The set-up of the selective amplification reactions was according the standard protocol with the exception that the above mentioned primers were used in the following combinations:

Combination 1: 00s31bio/00s41

Combination 2: 00s31bio/00s42

The selective amplification thermal cycling protocol was adapted for amplification of small fragments.

The selective thermal cycling protocol used was 13cycles (1 sec 94° C. and 5 sec 65° C.) in which the 65° C. is lowered to 56° C. followed by 23 cycles (1 sec 94° C. an sec 56° C.).

3. Preparing AFLP Reactions with Double Stranded Fragments.

After the selective amplification reaction in a 20 microliter volume with primer sequences described in section 2.3, an identical amount of 20 microliter selective amplification reagents was added to yield a 40 microliter total volume, and an extra cycle of PCR amplification was conducted according to the thermal cycle profile 1 sec 94° C. and 5 sec 56° C., to convert all AFLP fragments to double stranded DNA fragments.

4. Preparation of AFLP Oligonucleotide Tags.

Following the preparation of double stranded AFLP reactions as described in sections 2 and 3 above, a 5 microliter sample was taken from each tube and mixed with 5 microliter loading dye as a control prior to AFLP oligonucleotide tag preparation.

In a tube 5 microliter double stranded AFLP reaction product as mixed with 15 microliter, contains 5 microliter magnetic streptavidin coated beads in STEX, and incubated for 30 minutes at room temperature with gentle agitation. After this incubation the beads were concentrated with the magnetic particle concentrator and washed sequentially twice with 100 microliter STEX and once with 100 microliter ddH2O and reconstituted in 10 microliter ddH2O. The oligonucleotide tags are incubated for 5 minutes at 95° C. and after concentration on a magnetic particle concentrator the supernatant was quickly removed and transferred to another sample tube and 10 microliter loading dye was added. This sample was loaded on a sequence gel along side the earlier mentioned samples.

All above-mentioned samples were analysed on a denaturing 6% polyacrylamide sequence gel.

5. Results

FIG. 9 contains:

AFLP reactions prepared from templates prepared with the BcgI restriction enzyme:

Lane 1, 6, 7 and 12: contain a 10 basepair size ladder as a reference for fragment size; fragment sizes in basepairs are indicated on the right.

Lane 2: sample IR20, AFLP reaction 00s40/00s31bio in which the 00s40 primer was labelled with 33P.

Lane 3: sample 6383, AFLP reaction 00s40/00s31bio in which the 00s40 primer was labelled with 33P.

Lane 4: sample IR20, AFLP reaction 00s40/00s31bio in which the 00s40 primer was labelled with 33P followed by isolation of the oligonucleotide tags using magnetic streptavidin beads.

Lane 5: sample 6383, AFLP reaction 00s40/00s31bio in which the 00s40 primer was labelled with 33P followed by isolation of the oligonucleotide tags using magnetic streptavidin beads.

Lane 8: sample IR20, AFLP reaction 00s41/00s31bio in which the 00s41 primer was labelled with 33P.

Lane 9: sample 6383, AFLP reaction 00s41/00s31bio in which the 00s41 primer was labelled with 33P.

Lane 10: sample IR20, AFLP reaction 00s41/00s31bio in which the 00s41 primer was labelled with 33P followed by isolation of the oligonucleotide tags using magnetic streptavidin beads.

Lane 11: sample 6383, AFLP reaction 00s41/00s31bio in which the 00s41 primer was labelled with 33P followed by isolation of the oligonucleotide tags using magnetic streptavidin beads.

Figure 9:
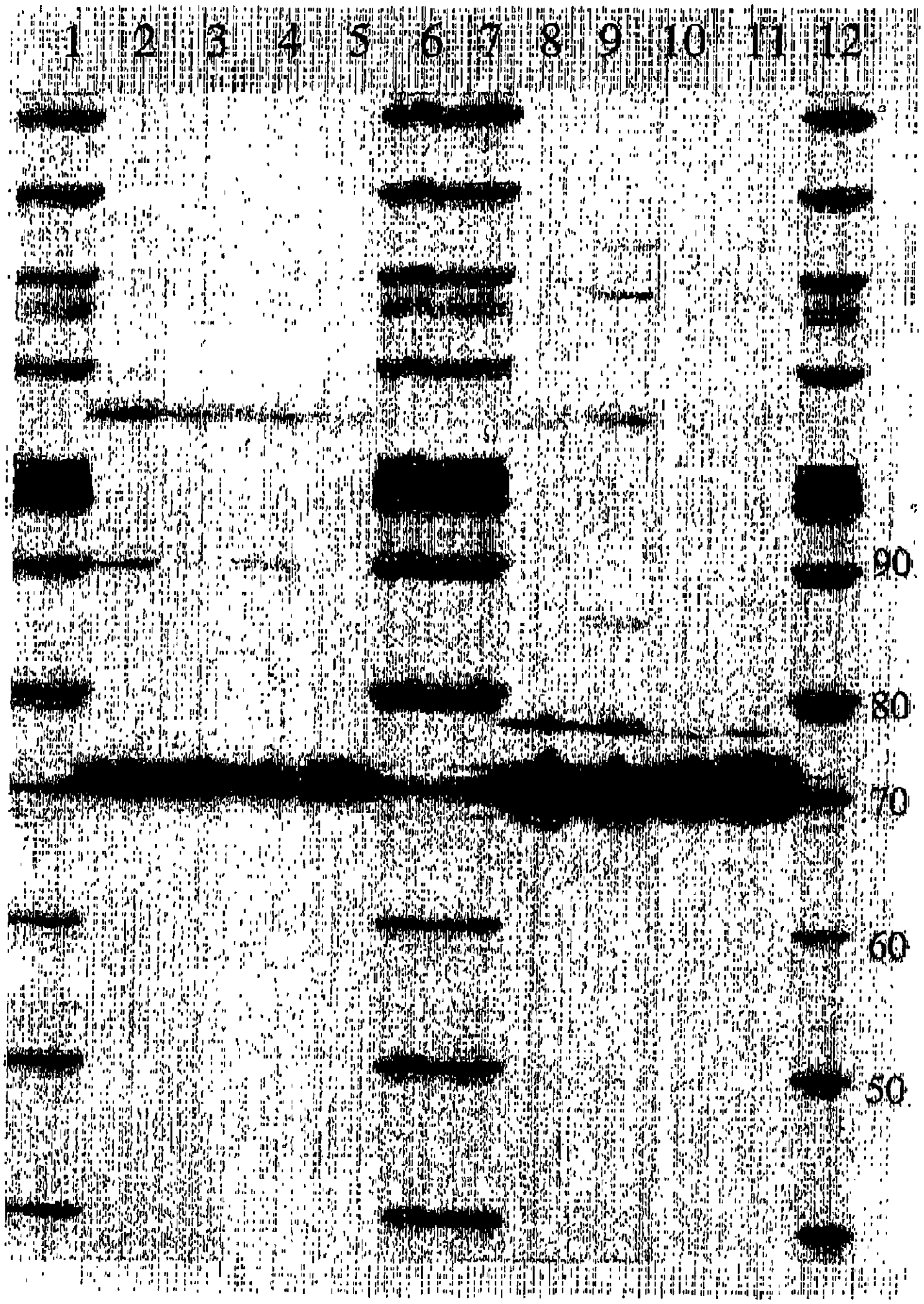
FIG. 9 shows AFLP reactions prepared from templates prepared with the BcgI restriction enzyme.

1. FIG. 9 shows:

1) The adapted amplification profile shows clear amplification of the 70 nucleotide fragments as shown in lanes 2, 3, 8 and 9.

2) After purification with streptavidin coated magnetic beads, fragments of 70 nucleotides are still present in lanes 4, 5, 10 and 11.

EXAMPLE VI

Representation of Alternative Method for Generating Oligonucleotide Tags with Fixed Length for e.g. Mass-Spectroscopic Analysis.

Starting with BcgI digested DNA fragments:

```
5' nnnnnnnnnnCGAnnnnnnTGCnnnnnnnnnnnn-3'
(SEQ ID NO. 81)

3' nnnnnnnnnnnnGCTnnnnnnACGnnnnnnnnnn-5'
(SEQ ID NO. 82)
```

Adapters X (xxxxxNN) and Y (yyyyNN), each with another core sequence are ligated onto the BcgI digested DNA fragments.

```
xxxxxNNnnnnnnnnnnCGAnnnnnnTGCnnnnnnnnnnnnYYYYY
(SEQ ID NO. 83)

XXXXXnnnnnnnnnnnnGCTnnnnnnACGnnnnnnnnnnNNyyyyy
(SEQ ID NO. 84)
```

The complexity of the DNA mixture is reduced through amplification with selective nucleotides. In the last amplification a primer is used with a 5'-biotin molecule.

```
Bio-xxxxATGnnnnnnnnnCGAnnnnnnTGCnnnnnnnnnTCGYYYYY
(SEQ ID NO. 85)

XXXXXTACnnnnnnnnnGCTnnnnnnACGnnnnnnnnnAGCyyyyy
(SEQ ID NO. 86)
```

Biotinylated fragments are purified from the amplification reaction using streptavidin coated magnetic beads.

```
Bio-xxxxxATGnnnnnnnnnCGAnnnnnnTGCnnnnnnnnnTCGYYYYY
(SEQ ID NO. 87)

XXXXXTACnnnnnnnnnGCTnnnnnnACGnnnnnnnnnAGCyyyyy
(SEQ ID NO. 88)
```

The fragments coupled on the magnetic beads are then digested. Only the short fragments coupled on the beads are digested as these are the only fragments which carry a recognition site for the restriction enzyme. In this way fragments of fixed length are released from the beads which are in the range for analysis on e.g. MALDI-TOF mass-spectroscopic analysis.

```
Bio-xxxxxAT   GnnnnnnnnnCGAnnnnnnTGCnnnnnnnnnTCG    YYYYY
(SEQ ID NO. 89)

  XXXXX     TACnnnnnnnnnGCTnnnnnnACGnnnnnnnnnA   GCyyyyy
(SEQ ID NO. 90)
```

The released short fragments are purified with an nucleotide removal kit.

```
GnnnnnnnnnCGAnnnnnnTGCnnnnnnnnnTCG    YYYYY
(SEQ ID NO. 91)

TACnnnnnnnnnGCTnnnnnnACGnnnnnnnnnA  GCyyyyy
(SEQ ID NO. 92)
```

The purified short fragments are analysed. Due to the presence of both strands of the BcgI fragments there is a each fragment will result in 2 peaks in a Mass spectroscopic analysis. If the presence of both strands is a problem, during the last amplification step a primer can be used which carries a biotin molecule on it's 5' prime end and carries nuclease resistant inter nucleotide bonds like phosphorothioate bonds. Such a primer would look like:

5'-biotin-xxxxxATG

The nucleotides A, T and G are separated by nuclease resistant bonds. When this primer is used the with streptavidin coated magnetic beads purified fragments can be cut with BcgI. One side of the fragment (which is coupled to the magnetic beads) will only be cut in one of the strand of the fragment whereas the other side of the fragment is cut in both strands. This results in the next fragments.

Bio-xxxxxATGnnnnnnnnnCGAnnnnnnTGCnnnnnnnnnTCG YYYYY
(SEQ ID NO. 93)

XXXXXTACnnnnnnnnnnnGCTnnnnnnACGnnnnnnnnnA GCyyyyy
(SEQ ID NO. 94)

The underlined nucleotides are separated but remain coupled to the other strand at this point. The beads are washed which removes the small fragments indicated on the right. When the resulting fragments on the beads are denatured e.g. by alkali or heat treatment, only two types of fragments are released. Shown in the same way as above these fragments look like below.

XXXXX TACnnnnnnnnnGCT-nnnnnnACGnnnnnnnnnA (SEQ ID NO. 95)

The fragments generated in this way are in the range for optimal detection by mass-spectroscopic analysis.

The skilled person will appreciate that the method of Example VI may equally be carried out using any of the other "double cutter" restriction endonucleases, i.e. restriction endonucleases which cut at two sites, different from the recognition site of the restriction endonuclease. Likewise, other affinity labels than the biotin label may be applied.

EXAMPLE VII

MaldiTOF-Mass Spectrophotometric Analysis of Oligonucleotide Tags from AFLP Reactions Generated with a MseI AFLP Adaptor and an Amplification Primer Containing a Type IIS Restriction Enzyme Site.

1. Preparation of AFLP Oligonucleotide Tags.

The oligonucleotide tags analysed were generated from the parental line 6383 used in example IV with the procedure stated in the example IV with the exception that a biotinylated primer containing a GsuI restriction site was used.

Figure 10:
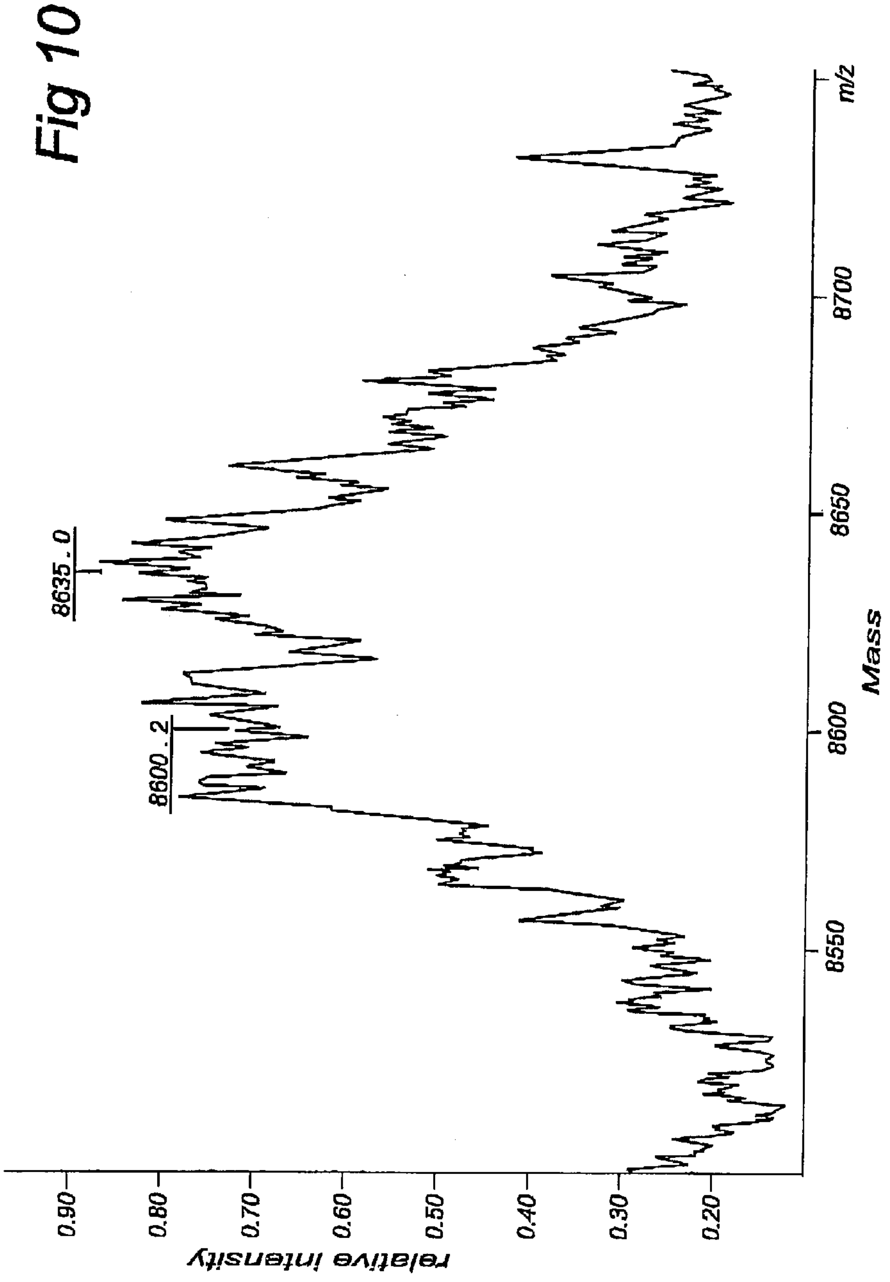
FIG. 10 is a mass spectrum from a Maldi TOF — Mass spectrophotometric analysis performed on oligonucleotide tags.

The oligonucleotide tags generated, were analysed by MaldiTOF-Mass spectrophotometry of which the result is shown in FIG. 10.

2. Results

FIG. 10 contains a mass spectrum from a MaldiTOF-Mass spectrophotometric analysis performed on the above generated oligonucleotide tags.

FIG. 10 shows:

1) Clear distinct peaks around the mass of 8615, which is the average mass of the oligonucleotide tags generated.

2) A total of 20–25 peaks are visible which represent 20–25 oligonucleotide tags with different masses.

The invention claimed is:

1. Method for detecting a restriction fragment, comprising the steps of:

(A) digesting a starting DNA, with one or more specific restriction endonucleases, to fragment said starting DNA into a series of restriction fragments;

(B) ligating the restriction fragments thus obtained with at least one double-stranded oligonucleotide adapter, one end of which can ligate with one or both of the ends of the restriction fragments, to thereby produce tagged restriction fragments of the starting DNA;

(C) contacting said tagged restriction fragments under hybridising conditions with at least one oligonucleotide primer;

(D) amplifying said tagged restriction fragments hybridised with said primers by PCR so as to cause further elongation of the hybridised primers along the restriction fragments of the starting DNA to which said primers hybridised; and (E) identifying or recovering the amplified or elongated DNA fragment thus obtained;

in which the detection of the amplified restriction fragments of step E) is carried out by mass spectroscopy, chromatography, or a combination thereof.

2. Method for detecting a restriction fragment, comprising the steps of:

(A) digesting a starting DNA, with one or more specific restriction endonucleases, to fragment said starting DNA into a series of restriction fragments;

(B) ligating the restriction fragments thus obtained with one double-stranded oligonucleotide adapter to thereby produce tagged restriction fragments of the starting DNA;

(C) contacting said tagged restriction fragments under hybridising conditions with at least one oligonucleotide primer;

(D) amplifying said tagged restriction fragments hybridised with said primers by PCR so as to cause further elongation of the hybridised primers along the restriction fragments of the starting DNA to which said primers hybridised; and (E) identifying or recovering the amplified or elongated DNA fragment thus obtained;

in which:

the adapter used in step B) comprises within its sequence a recognition site for a IIS restriction endonuclease;

and in which:

step E) comprises the steps of:

d) restricting the ligated dsDNA with the restriction endonuclease of the IIS type which recognizes the recognition site within the adapter so as to obtain at least a first and a second IIS-restricted dsDNA;

e1) generating at least one ssDNA from at least one of the amplified restriction fragments obtained in step D);

e2) detecting the at least one ssDNA generated in step e1).

3. Method according to claim 2, in which the at least one ss DNA generated in step e1) is detected in step e2) by mass spectroscopy, chromatography, or a combination thereof.

4. Method according to claim 2, in which at least one of the primers used in step (C) is resistant to an exonuclease.

5. Method according to claim 2, in which in step e1), the mixture of amplified restriction fragments obtained in step D) is treated with an exonuclease, optionally after heat denaturation.

6. Method for generating, and optionally detecting, an oligonucleotide that is specific for a starting nucleic acid, comprising the steps of:

a) providing a dsDNA;

b) restricting the dsDNA with at least one restriction endonuclease that restricts the dsDNA at two sites different from the recognition site of said restriction endonuclease, so as to provide a mixture of restricted fragments, said mixture comprising one or more fragments that contain the recognition site of the restriction endonuclease and one or more fragments that do not contain the recognition site of the restriction endonuclease used;

c) ligating the first dsDNA to a second dsDNA, so as to provide a ligated dsDNA;

d) amplifying the mixture of fragments obtained in step c);

e) detecting at least one of the amplified fragments obtained in step d).

7. Method according to claim 6, in which, in step (e), one or more of the amplified fragments that contain the recognition site of the restriction endonuclease are detected, optionally after isolation of these fragments from the amplified mixture obtained in step d).

8. Method according to claim 6, in which detection step (e) is carried out on ligated dsDNA obtained in step (c), optionally after specific isolation of one or more the ligated dsDNA fragments.

9. Method according to claim 6, in which in the amplification step d), a biotinylated primer is used.

10. Method according to claim 6, in which in the amplification step d), an exonuclease resistant primer is used.

11. Method according to claim 10, in which a ssDNA is generated by treating a strands of the type IIS restricted fragments obtained in step d) with an exonuclease.

12. Method according to claim 6, in which the amplification of step c) is carried out using primers that can hybridise with at least part of the nucleotide sequence of the adapters ligated to the ends of the restriction fragments to be amplified and which optionally comprise one or more selective bases at the 3'-end.

13. Method according to claim 6, in which the detection of step d) is carried out by mass spectroscopy or chromatography or a combination thereof.

14. Method for generating, and optionally detecting, an oligonucleotide that is specific for a starting nucleic acid, comprising the steps of:

a) providing a first dsDNA;

b) restricting the first dsDNA with at least one restriction endonuclease that restricts the first dsDNA at two sites different from the recognition site of the restriction endonuclease, so as to provide a mixture of restricted fragments, the mixture comprising one or more fragments that contain the recognition site of the restriction endonuclease and one or more fragments that do not contain the recognition site of the restriction endonuclease;

c) ligating the restricted fragments of the first dsDNA as obtained in (b) to a second dsDNA, in which the second dsDNA contains a recognition sequence for a type IIS restriction endonuclease in close proximity to the end ligating to the restricted fragment of the first dsDNA, so as to provide a ligated dsDNA;

d) amplifying the ligated dsDNA obtained in (c);

e) digestion of the amplified fragments obtained in (d) with the type IIS restriction endonuclease;

f) detecting a fragment obtained in (e).

15. Method for generating, and optionally detecting, an oligonucleotide that is specific for a starting nucleic acid, comprising the steps of:

a) providing a first dsDNA;

b) restricting the first dsDNA with at least one restriction endonuclease that restricts the first dsDNA at two sites different from the recognition site of the restriction endonuclease, so as to provide a mixture of restricted fragments, the mixture comprising one or more fragments that contain the recognition site of the restriction endonuclease and one or more fragments that do not contain the recognition site of the restriction endonuclease;

c) ligating ds DNA adapter sequences to both ends of the restriction fragments, so as to provide a ligated dsDNA;

d) amplifying the ligated dsDNA obtained in (c);

e) digestion of the amplified fragments obtained in (d) with the restriction endonuclease;

f) detecting a fragment obtained in (e).

16. Method according to claim 15, in which in step (f) one or more of the amplified fragments that contain the recognition site of the restriction endonuclease are detected, optionally after specific isolation of at least one of the amplified fragments.

* * * * *

SEQUENCE LISTING

```
<160> NUMBER OF SEQ ID NOS: 95

<210> SEQ ID NO 1
<211> LENGTH: 17
<212> TYPE: DNA
<213> ORGANISM: Artificial
<220> FEATURE:
<223> OTHER INFORMATION: synthetic

<400> SEQUENCE: 1

ctcgtagact gcgtacc                                       17


<210> SEQ ID NO 2
<211> LENGTH: 18
<212> TYPE: DNA
<213> ORGANISM: Artificial
<220> FEATURE:
<223> OTHER INFORMATION: synthetic

<400> SEQUENCE: 2

aattggtacg cagtctac                                      18


<210> SEQ ID NO 3
<211> LENGTH: 17
<212> TYPE: DNA
<213> ORGANISM: Artificial
<220> FEATURE:
<223> OTHER INFORMATION: synthetic
```

-continued

<400> SEQUENCE: 3
gactgcgtac caattca 17

<210> SEQ ID NO 4
<211> LENGTH: 19
<212> TYPE: DNA
<213> ORGANISM: Artificial
<220> FEATURE:
<223> OTHER INFORMATION: synthetic

<400> SEQUENCE: 4
gacctgcgta ccaattcac 19

<210> SEQ ID NO 5
<211> LENGTH: 16
<212> TYPE: DNA
<213> ORGANISM: Artificial
<220> FEATURE:
<223> OTHER INFORMATION: synthetic

<400> SEQUENCE: 5
gacgatgagt cctgag 16

<210> SEQ ID NO 6
<211> LENGTH: 14
<212> TYPE: DNA
<213> ORGANISM: Artificial
<220> FEATURE:
<223> OTHER INFORMATION: synthetic

<400> SEQUENCE: 6
tactcaggac tcat 14

<210> SEQ ID NO 7
<211> LENGTH: 17
<212> TYPE: DNA
<213> ORGANISM: Artificial
<220> FEATURE:
<223> OTHER INFORMATION: synthetic

<400> SEQUENCE: 7
gatgagtcct gagtaac 17

<210> SEQ ID NO 8
<211> LENGTH: 19
<212> TYPE: DNA
<213> ORGANISM: Artificial
<220> FEATURE:
<223> OTHER INFORMATION: synthetic

<400> SEQUENCE: 8
gatgagtcct gagtaacaa 19

<210> SEQ ID NO 9
<211> LENGTH: 16
<212> TYPE: DNA
<213> ORGANISM: Artificial
<220> FEATURE:
<223> OTHER INFORMATION: synthetic

<400> SEQUENCE: 9
gacgatgagt ctggag 16

<210> SEQ ID NO 10
<211> LENGTH: 14

-continued

<212> TYPE: DNA
<213> ORGANISM: Artificial
<220> FEATURE:
<223> OTHER INFORMATION: synthetic

<400> SEQUENCE: 10
tactccagac tcat 14

<210> SEQ ID NO 11
<211> LENGTH: 20
<212> TYPE: DNA
<213> ORGANISM: Artificial
<220> FEATURE:
<223> OTHER INFORMATION: synthetic

<400> SEQUENCE: 11
gacgatgagt ctggagtaac 20

<210> SEQ ID NO 12
<211> LENGTH: 22
<212> TYPE: DNA
<213> ORGANISM: Artificial
<220> FEATURE:
<223> OTHER INFORMATION: synthetic

<400> SEQUENCE: 12
gacgatgagt ctggagtaac aa 22

<210> SEQ ID NO 13
<211> LENGTH: 16
<212> TYPE: DNA
<213> ORGANISM: Artificial
<220> FEATURE:
<223> OTHER INFORMATION: synthetic

<400> SEQUENCE: 13
gacgatgagt gtgcag 16

<210> SEQ ID NO 14
<211> LENGTH: 14
<212> TYPE: DNA
<213> ORGANISM: Artificial
<220> FEATURE:
<223> OTHER INFORMATION: synthetic

<400> SEQUENCE: 14
tactgcacac tcat 14

<210> SEQ ID NO 15
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature
<222> LOCATION: (23)..(36)
<223> OTHER INFORMATION: n is a, c, g, or t

<400> SEQUENCE: 15
nnnnnnnnnn nnnnnngtgc agnnnnnnnn nnnnnn 36

<210> SEQ ID NO 16

-continued

<211> LENGTH: 22
<212> TYPE: DNA
<213> ORGANISM: Artificial
<220> FEATURE:
<223> OTHER INFORMATION: synthetic

<400> SEQUENCE: 16
gacgatgagt gtgcagtaac aa 22

<210> SEQ ID NO 17
<211> LENGTH: 19
<212> TYPE: DNA
<213> ORGANISM: Artificial
<220> FEATURE:
<223> OTHER INFORMATION: synthetic

<400> SEQUENCE: 17
gatgagtcct gagtaacat 19

<210> SEQ ID NO 18
<211> LENGTH: 22
<212> TYPE: DNA
<213> ORGANISM: Artificial
<220> FEATURE:
<223> OTHER INFORMATION: synthetic

<400> SEQUENCE: 18
gacgatgagt ctggagtaac ag 22

<210> SEQ ID NO 19
<211> LENGTH: 22
<212> TYPE: DNA
<213> ORGANISM: Artificial
<220> FEATURE:
<223> OTHER INFORMATION: synthetic

<400> SEQUENCE: 19
gacgatgagt gtgcagtaac at 22

<210> SEQ ID NO 20
<211> LENGTH: 19
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (18)..(19)
<223> OTHER INFORMATION: n is a, c, g, or t

<400> SEQUENCE: 20
ctcgtagact gcgtaccnn 19

<210> SEQ ID NO 21
<211> LENGTH: 17
<212> TYPE: DNA
<213> ORGANISM: Artificial
<220> FEATURE:
<223> OTHER INFORMATION: synthetic

<400> SEQUENCE: 21
ggtacgcagt ctacgag 17

<210> SEQ ID NO 22
<211> LENGTH: 19
<212> TYPE: DNA
<213> ORGANISM: Artificial

-continued

<220> FEATURE:
<223> OTHER INFORMATION: synthetic
<220> FEATURE:
<221> NAME/KEY: misc_feature
<222> LOCATION: (18)..(19)
<223> OTHER INFORMATION: n is a, c, g, or t

<400> SEQUENCE: 22
gacgatgagt cctgagann 19

<210> SEQ ID NO 23
<211> LENGTH: 17
<212> TYPE: DNA
<213> ORGANISM: Artificial
<220> FEATURE:
<223> OTHER INFORMATION: synthetic

<400> SEQUENCE: 23
tctcaggact catcgtc 17

<210> SEQ ID NO 24
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (18)..(18)
<223> OTHER INFORMATION: n is a, c, g, or t

<400> SEQUENCE: 24
ctcgtagact gcgtaccn 18

<210> SEQ ID NO 25
<211> LENGTH: 19
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (19)..(19)
<223> OTHER INFORMATION: n is a, c, g, or t

<400> SEQUENCE: 25
gacgatgagt cctgagacn 19

<210> SEQ ID NO 26
<211> LENGTH: 19
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (18)..(19)
<223> OTHER INFORMATION: n is a, c, g, or t

<400> SEQUENCE: 26
ctcgtagact gcgtaccnn 19

<210> SEQ ID NO 27
<211> LENGTH: 20
<212> TYPE: DNA
<213> ORGANISM: Artificial
<220> FEATURE:
<223> OTHER INFORMATION: synthetic
<220> FEATURE:

-continued

<221> NAME/KEY: misc_feature
<222> LOCATION: (19)..(20)
<223> OTHER INFORMATION: n is a, c, g, or t

<400> SEQUENCE: 27
gacgatgagt cctgagacnn 20

<210> SEQ ID NO 28
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (18)..(20)
<223> OTHER INFORMATION: n is a, c, g, or t

<400> SEQUENCE: 28
ctcgtagact gcgtaccnnn 20

<210> SEQ ID NO 29
<211> LENGTH: 21
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (19)..(21)
<223> OTHER INFORMATION: n is a, c, g, or t

<400> SEQUENCE: 29
gacgatgagt cctgagacnn n 21

<210> SEQ ID NO 30
<211> LENGTH: 19
<212> TYPE: DNA
<213> ORGANISM: Artificial
<220> FEATURE:
<223> OTHER INFORMATION: synthetic

<400> SEQUENCE: 30
gatgagtctg gagtaacac 19

<210> SEQ ID NO 31
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (3)..(3)
<223> OTHER INFORMATION: g is represented by a bioT (biotin molecule)
group.

<400> SEQUENCE: 31
gagagtgtgc agtaacac 18

<210> SEQ ID NO 32
<211> LENGTH: 19
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (18)..(19)

-continued

<223> OTHER INFORMATION: n is a, c, g, or t

<400> SEQUENCE: 32
ctcgtagact gcgtaccnn 19

<210> SEQ ID NO 33
<211> LENGTH: 17
<212> TYPE: DNA
<213> ORGANISM: Artificial
<220> FEATURE:
<223> OTHER INFORMATION: synthetic

<400> SEQUENCE: 33
ggtacgcagt ctacgag 17

<210> SEQ ID NO 34
<211> LENGTH: 19
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (18)..(19)
<223> OTHER INFORMATION: n is a, c, g, or t

<400> SEQUENCE: 34
gacgatgagt cctgagann 19

<210> SEQ ID NO 35
<211> LENGTH: 17
<212> TYPE: DNA
<213> ORGANISM: Artificial
<220> FEATURE:
<223> OTHER INFORMATION: synthetic

<400> SEQUENCE: 35
tctcaggact catcgtc 17

<210> SEQ ID NO 36
<211> LENGTH: 18
<212> TYPE: DNA
<213> ORGANISM: Artificial
<220> FEATURE:
<223> OTHER INFORMATION: synthetic

<400> SEQUENCE: 36
ctcgtagact gcgtacca 18

<210> SEQ ID NO 37
<211> LENGTH: 19
<212> TYPE: DNA
<213> ORGANISM: Artificial
<220> FEATURE:
<223> OTHER INFORMATION: synthetic

<400> SEQUENCE: 37
gacgatgagt cctgagacc 19

<210> SEQ ID NO 38
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature -continued
<222> LOCATION: (1)..(1)
<223> OTHER INFORMATION: "c" is represented by a bio group.

<400> SEQUENCE: 38
ctcgtagact gcgtaccaca 20

<210> SEQ ID NO 39
<211> LENGTH: 21
<212> TYPE: DNA
<213> ORGANISM: Artificial
<220> FEATURE:
<223> OTHER INFORMATION: synthetic

<400> SEQUENCE: 39
gacgatgagt cctgagacca c 21

<210> SEQ ID NO 40
<211> LENGTH: 21
<212> TYPE: DNA
<213> ORGANISM: Artificial
<220> FEATURE:
<223> OTHER INFORMATION: synthetic

<400> SEQUENCE: 40
gacgatgagt cctgagacca g 21

<210> SEQ ID NO 41
<211> LENGTH: 26
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (7)..(26)
<223> OTHER INFORMATION: n is a, c, g, or t

<400> SEQUENCE: 41
tccracnnnn nnnnnnnnnn nnnnnn 26

<210> SEQ ID NO 42
<211> LENGTH: 24
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(18)
<223> OTHER INFORMATION: n is a, c, g, or t

<400> SEQUENCE: 42
nnnnnnnnnn nnnnnnnngt ygga 24

<210> SEQ ID NO 43
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (7)..(22)
<223> OTHER INFORMATION: n is a, c, g, or t

<400> SEQUENCE: 43
ctgaagnnnn nnnnnnnnnn nn 22

-continued

<210> SEQ ID NO 44
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: n is a, c, g, or t

<400> SEQUENCE: 44
nnnnnnnnnn nnnncttcag 20

<210> SEQ ID NO 45
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (7)..(22)
<223> OTHER INFORMATION: n is a, c, g, or t

<400> SEQUENCE: 45
gtgcagnnnn nnnnnnnnnn nn 22

<210> SEQ ID NO 46
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: n is a, c, g, or t

<400> SEQUENCE: 46
nnnnnnnnnn nnnnctgcac 20

<210> SEQ ID NO 47
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (7)..(22)
<223> OTHER INFORMATION: n is a, c, g, or t

<400> SEQUENCE: 47
ctggagnnnn nnnnnnnnnn nn 22

<210> SEQ ID NO 48
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: n is a, c, g, or t

<400> SEQUENCE: 48
nnnnnnnnnn nnnnctccag 20

-continued

<210> SEQ ID NO 49
<211> LENGTH: 17
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (7)..(17)
<223> OTHER INFORMATION: n is a, c, g, or t

<400> SEQUENCE: 49
cacccannnn nnnnnnn 17

<210> SEQ ID NO 50
<211> LENGTH: 15
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(9)
<223> OTHER INFORMATION: n is a, c, g, or t

<400> SEQUENCE: 50
nnnnnnnnnt gggtg 15

<210> SEQ ID NO 51
<211> LENGTH: 17
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (7)..(17)
<223> OTHER INFORMATION: n is a, c, g, or t

<400> SEQUENCE: 51
caarcannnn nnnnnnn 17

<210> SEQ ID NO 52
<211> LENGTH: 15
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(9)
<223> OTHER INFORMATION: n is a, c, g, or t

<400> SEQUENCE: 52
nnnnnnnnnt gyttg 15

<210> SEQ ID NO 53
<211> LENGTH: 15
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (6)..(15)
<223> OTHER INFORMATION: n is a, c, g, or t

<400> SEQUENCE: 53

-continued

```
gggacnnnnn nnnnn                                                       15


<210> SEQ ID NO 54
<211> LENGTH: 19
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(14)
<223> OTHER INFORMATION: n is a, c, g, or t

<400> SEQUENCE: 54

nnnnnnnnnn nnnngtccc                                                   19


<210> SEQ ID NO 55
<211> LENGTH: 14
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (6)..(14)
<223> OTHER INFORMATION: n is a, c, g, or t

<400> SEQUENCE: 55

ggatgnnnnn nnnn                                                        14


<210> SEQ ID NO 56
<211> LENGTH: 18
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(13)
<223> OTHER INFORMATION: n is a, c, g, or t

<400> SEQUENCE: 56

nnnnnnnnnn nnncatcc                                                    18


<210> SEQ ID NO 57
<211> LENGTH: 13
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (6)..(13)
<223> OTHER INFORMATION: n is a, c, g, or t

<400> SEQUENCE: 57

gcagcnnnnn nnn                                                         13


<210> SEQ ID NO 58
<211> LENGTH: 17
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: n is a, c, g, or t

<400> SEQUENCE: 58
```

-continued

```
nnnnnnnnnn nngctgc                                                17


<210> SEQ ID NO 59
<211> LENGTH: 38
<212> TYPE: DNA
<213> ORGANISM: Artificial
<220> FEATURE:
<223> OTHER INFORMATION: BaeI restriction endonuclease recognition
      sequence
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (18)..(21)
<223> OTHER INFORMATION: n is a, c, g, or t
<220> FEATURE:
<221> NAME/KEY: misc_feature
<222> LOCATION: (27)..(38)
<223> OTHER INFORMATION: n is a, c, g, or t

<400> SEQUENCE: 59

nnnnnnnnnn nnnnnacnnn ngtaycnnnn nnnnnnnn                         38


<210> SEQ ID NO 60
<211> LENGTH: 38
<212> TYPE: DNA
<213> ORGANISM: Artificial
<220> FEATURE:
<223> OTHER INFORMATION: BaeI restriction endonuclease recognition
      sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (18)..(21)
<223> OTHER INFORMATION: n is a, c, g, or t
<220> FEATURE:
<221> NAME/KEY: misc_feature
<222> LOCATION: (24)..(38)
<223> OTHER INFORMATION: n is a, c, g, or t

<400> SEQUENCE: 60

nnnnnnnnnn nngrtacnnn ngtnnnnnnn nnnnnnnn                         38


<210> SEQ ID NO 61
<211> LENGTH: 36
<212> TYPE: DNA
<213> ORGANISM: Artificial
<220> FEATURE:
<223> OTHER INFORMATION: BcgI restriction endonuclease recognition
      sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(36)
<223> OTHER INFORMATION: n is a, c, g, or t

<400> SEQUENCE: 61

nnnnnnnnnn nncgannnnn ntgcnnnnnn nnnnnn                           36
```

-continued

```
<210> SEQ ID NO 62
<211> LENGTH: 36
<212> TYPE: DNA
<213> ORGANISM: Artificial
<220> FEATURE:
<223> OTHER INFORMATION: BcgI restriction endonuclease recognition
      sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(36)
<223> OTHER INFORMATION: n is a, c, g, or t

<400> SEQUENCE: 62

nnnnnnnnnn nngcannnnn ntcgnnnnnn nnnnnn                              36


<210> SEQ ID NO 63
<211> LENGTH: 37
<212> TYPE: DNA
<213> ORGANISM: Artificial
<220> FEATURE:
<223> OTHER INFORMATION: BpII restriction endonuclease recognition
      sequence
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (17)..(21)
<223> OTHER INFORMATION: n is a, c, g, or t
<220> FEATURE:
<221> NAME/KEY: misc_feature
<222> LOCATION: (25)..(37)
<223> OTHER INFORMATION: n is a, c, g, or t

<400> SEQUENCE: 63

nnnnnnnnnn nnngagnnnn nctcnnnnnn nnnnnnn                             37


<210> SEQ ID NO 64
<211> LENGTH: 37
<212> TYPE: DNA
<213> ORGANISM: Artificial
<220> FEATURE:
<223> OTHER INFORMATION: BpII restriction endonuclease recognition
      sequence
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (17)..(21)
<223> OTHER INFORMATION: n is a, c, g, or t
<220> FEATURE:
<221> NAME/KEY: misc_feature
<222> LOCATION: (25)..(37)
<223> OTHER INFORMATION: n is a, c, g, or t

<400> SEQUENCE: 64

nnnnnnnnnn nnngagnnnn nctcnnnnnn nnnnnnn                             37


<210> SEQ ID NO 65
<211> LENGTH: 37
<212> TYPE: DNA
<213> ORGANISM: Artificial
```

-continued

<220> FEATURE:
<223> OTHER INFORMATION: Bsp24I restriction endonuclease recognition
sequence
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (17)..(22)
<223> OTHER INFORMATION: n is a, c, g, or t
<220> FEATURE:
<221> NAME/KEY: misc_feature
<222> LOCATION: (26)..(37)
<223> OTHER INFORMATION: n is a, c, g, or t

<400> SEQUENCE: 65
nnnnnnnnnn nnngacnnnn nntggnnnnn nnnnnnn 37

<210> SEQ ID NO 66
<211> LENGTH: 37
<212> TYPE: DNA
<213> ORGANISM: Artificial
<220> FEATURE:
<223> OTHER INFORMATION: Bsp24I restriction endonuclease recognition
sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(37)
<223> OTHER INFORMATION: n is a, c, g, or t

<400> SEQUENCE: 66
nnnnnnnnnn nnccannnnn ngtcnnnnnn nnnnnnn 37

<210> SEQ ID NO 67
<211> LENGTH: 40
<212> TYPE: DNA
<213> ORGANISM: Artificial
<220> FEATURE:
<223> OTHER INFORMATION: CjeI restriction endonuclease recognition
sequence
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (18)..(23)
<223> OTHER INFORMATION: n is a, c, g, or t
<220> FEATURE:
<221> NAME/KEY: misc_feature
<222> LOCATION: (26)..(40)
<223> OTHER INFORMATION: n is a, c, g, or t

<400> SEQUENCE: 67
nnnnnnnnnn nnnnccannn nnngtnnnnn nnnnnnnnnn 40

<210> SEQ ID NO 68
<211> LENGTH: 41
<212> TYPE: DNA
<213> ORGANISM: Artificial
<220> FEATURE:
<223> OTHER INFORMATION: CjeI restriction endonuclease recognition
sequence
<220> FEATURE:

-continued

<221> NAME/KEY: misc_feature
<222> LOCATION: (1)..(16)
<223> OTHER INFORMATION: n is a, c, g, or t
<220> FEATURE:
<221> NAME/KEY: misc_feature
<222> LOCATION: (19)..(24)
<223> OTHER INFORMATION: n is a, c, g, or t
<220> FEATURE:
<221> NAME/KEY: misc_feature
<222> LOCATION: (28)..(41)
<223> OTHER INFORMATION: n is a, c, g, or t

<400> SEQUENCE: 68
nnnnnnnnnn nnnnnnacnn nnnntggnnn nnnnnnnnnn n 41

<210> SEQ ID NO 69
<211> LENGTH: 38
<212> TYPE: DNA
<213> ORGANISM: Artificial
<220> FEATURE:
<223> OTHER INFORMATION: CjePI restriction endonuclease recognition sequence
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (16)..(22)
<223> OTHER INFORMATION: n is a, c, g, or t
<220> FEATURE:
<221> NAME/KEY: misc_feature
<222> LOCATION: (25)..(38)
<223> OTHER INFORMATION: n is a, c, g, or t

<400> SEQUENCE: 69
nnnnnnnnnn nnccannnnn nntcnnnnnn nnnnnnnn 38

<210> SEQ ID NO 70
<211> LENGTH: 38
<212> TYPE: DNA
<213> ORGANISM: Artificial
<220> FEATURE:
<223> OTHER INFORMATION: CjePI restriction endonuclease recognition sequence
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: misc_feature
<222> LOCATION: (17)..(23)
<223> OTHER INFORMATION: n is a, c, g, or t
<220> FEATURE:
<221> NAME/KEY: misc_feature
<222> LOCATION: (27)..(38)
<223> OTHER INFORMATION: n is a, c, g, or t

<400> SEQUENCE: 70
nnnnnnnnnn nnnngannnn nnntggnnnn nnnnnnnn 38

<210> SEQ ID NO 71
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature -continued
<222> LOCATION: (23)..(36)
<223> OTHER INFORMATION: n is a, c, g, or t

<400> SEQUENCE: 71
nnnnnnnnnn nnnnnnctgg agnnnnnnnn nnnnnn 36

<210> SEQ ID NO 72
<211> LENGTH: 34
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (14)..(19)
<223> OTHER INFORMATION: n is a, c, g, or t
<220> FEATURE:
<221> NAME/KEY: misc_feature
<222> LOCATION: (23)..(34)
<223> OTHER INFORMATION: n is a, c, g, or t

<400> SEQUENCE: 72
nnnnnnnnnn cgannnnnnt gcnnnnnnnn nnnn 34

<210> SEQ ID NO 73
<211> LENGTH: 34
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (14)..(19)
<223> OTHER INFORMATION: n is a, c, g, or t
<220> FEATURE:
<221> NAME/KEY: misc_feature
<222> LOCATION: (23)..(34)
<223> OTHER INFORMATION: n is a, c, g, or t

<400> SEQUENCE: 73
nnnnnnnnnn cgannnnnnt cgnnnnnnnn nnnn 34

<210> SEQ ID NO 74
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(36)
<223> OTHER INFORMATION: n is a, c, g, or t

<400> SEQUENCE: 74
nnnnnnnnnn nncgannnnn ntgcnnnnnn nnnnnn 36

-continued

<210> SEQ ID NO 75
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(36)
<223> OTHER INFORMATION: n is a, c, g, or t

<400> SEQUENCE: 75
nnnnnnnnnn nngcannnnn ntcgnnnnnn nnnnnn 36

<210> SEQ ID NO 76
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 76
atgnnnnnnn nncgannnnn ntcgnnnnnn nnntcg 36

<210> SEQ ID NO 77
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 77
gcannnnnnn nngcannnnn ntcgnnnnnn nnncat 36

<210> SEQ ID NO 78
<211> LENGTH: 36
<212> TYPE: DNA
<213> ORGANISM: Artificial
<220> FEATURE:
<223> OTHER INFORMATION: synthetic -continued
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 78
tacnnnnnnn nngctnnnnn nacgnnnnnn nnnagc 36

<210> SEQ ID NO 79
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature
<222> LOCATION: (23)..(36)
<223> OTHER INFORMATION: n is a, c, g, or t

<400> SEQUENCE: 79
nnnnnnnnnn nnnnnnctgg agnnnnnnnn nnnnnn 36

<210> SEQ ID NO 80
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(16)
<223> OTHER INFORMATION: n is a, c, g, or t
<220> FEATURE:
<221> NAME/KEY: misc_feature
<222> LOCATION: (23)..(36)
<223> OTHER INFORMATION: n is a, c, g, or t

<400> SEQUENCE: 80
nnnnnnnnnn nnnnnngtgc agnnnnnnnn nnnnnn 36

<210> SEQ ID NO 81
<211> LENGTH: 34
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (14)..(19)
<223> OTHER INFORMATION: n is a, c, g, or t
<220> FEATURE:
<221> NAME/KEY: misc_feature
<222> LOCATION: (23)..(34)
<223> OTHER INFORMATION: n is a, c, g, or t

<400> SEQUENCE: 81

-continued nnnnnnnnnn cgannnnnnt gcnnnnnnnn nnnn 34

<210> SEQ ID NO 82
<211> LENGTH: 34
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (14)..(19)
<223> OTHER INFORMATION: n is a, c, g, or t
<220> FEATURE:
<221> NAME/KEY: misc_feature
<222> LOCATION: (23)..(34)
<223> OTHER INFORMATION: n is a, c, g, or t

<400> SEQUENCE: 82
nnnnnnnnnn gcannnnnnt cgnnnnnnnn nnnn 34

<210> SEQ ID NO 83
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(36)
<223> OTHER INFORMATION: n is a, c, g, or t

<400> SEQUENCE: 83
nnnnnnnnnn nncgannnnn ntgcnnnnnn nnnnnn 36

<210> SEQ ID NO 84
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(36)
<223> OTHER INFORMATION: n is a, c, g, or t

<400> SEQUENCE: 84
nnnnnnnnnn nngcannnnn ntcgnnnnnn nnnnnn 36

<210> SEQ ID NO 85
<211> LENGTH: 36
<212> TYPE: DNA
<213> ORGANISM: Artificial

-continued

<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 85
atgnnnnnnn nncgannnnn ntgcnnnnnn nnntcg 36

<210> SEQ ID NO 86
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 86
cgannnnnnn nngcannnnn ntcgnnnnnn nnncat 36

<210> SEQ ID NO 87
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 87
atgnnnnnnn nncgannnnn ntgcnnnnnn nnntcg 36

<210> SEQ ID NO 88
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:

-continued

<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 88
cgannnnnnn nngcannnnn ntcgnnnnnn nnncat 36

<210> SEQ ID NO 89
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 89
atgnnnnnnn nncgannnnn ntgcnnnnnn nnntcg 36

<210> SEQ ID NO 90
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 90
cgannnnnnn nngcannnnn ntcgnnnnnn nnncat 36

<210> SEQ ID NO 91
<211> LENGTH: 34
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (2)..(10)
<223> OTHER INFORMATION: n is a, c, g, or t
<220> FEATURE:
<221> NAME/KEY: misc_feature
<222> LOCATION: (14)..(19)
<223> OTHER INFORMATION: n is a, c, g, or t
<220> FEATURE:
<221> NAME/KEY: misc_feature
<222> LOCATION: (23)..(31)
<223> OTHER INFORMATION: n is a, c, g, or t -continued

<400> SEQUENCE: 91
gnnnnnnnnn cgannnnnnt gcnnnnnnnn ntcg 34

<210> SEQ ID NO 92
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 92
cgannnnnnn nngcannnnn ntcgnnnnnn nnncat 36

<210> SEQ ID NO 93
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 93
atgnnnnnnn nncgannnnn ntgcnnnnnn nnntcg 36

<210> SEQ ID NO 94
<211> LENGTH: 36
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 94
cgannnnnnn nngcannnnn ntcgnnnnnn nnncat 36

<210> SEQ ID NO 95

-continued

```
<211> LENGTH: 34
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: n is a, c, g, or t
<220> FEATURE:
<221> NAME/KEY: misc_feature
<222> LOCATION: (16)..(21)
<223> OTHER INFORMATION: n is a, c, g, or t
<220> FEATURE:
<221> NAME/KEY: misc_feature
<222> LOCATION: (25)..(33)
<223> OTHER INFORMATION: n is a, c, g, or t

<400> SEQUENCE: 95

tacnnnnnnn nngctnnnnn nacgnnnnnn nnna                               34
```